US008225796B2

(12) United States Patent
Davenport et al.

(10) Patent No.: US 8,225,796 B2
(45) Date of Patent: Jul. 24, 2012

(54) RESPIRATORY THERAPY SYSTEM INCLUDING A NASAL CANNULA ASSEMBLY

(75) Inventors: James M. Davenport, Fallbrook, CA (US); James N. Curti, Bakersfield, CA (US); Barry Crandall, Bakersfield, CA (US); Peter W. Salter, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 1186 days.

(21) Appl. No.: 10/566,305

(22) PCT Filed: Jul. 27, 2004

(86) PCT No.: PCT/US2004/024291
§ 371 (c)(1),
(2), (4) Date: Feb. 23, 2006

(87) PCT Pub. No.: WO2005/011556
PCT Pub. Date: Feb. 10, 2005

(65) Prior Publication Data
US 2008/0051674 A1 Feb. 28, 2008

Related U.S. Application Data

(60) Provisional application No. 60/490,577, filed on Jul. 28, 2003, provisional application No. 60/528,008, filed on Dec. 9, 2003.

(51) Int. Cl.
*A61M 16/00* (2006.01)
*A62B 7/00* (2006.01)

(52) U.S. Cl. ......... 128/207.18; 128/204.18; 128/204.21; 128/204.22; 128/204.23; 128/205.23

(58) Field of Classification Search ............. 128/207.18, 128/200.24, 200.26, 202.27, 203.12, 23.22, 128/204.18
See application file for complete search history.

(56) References Cited

U.S. PATENT DOCUMENTS
2,135,052 A 11/1938 Rose
(Continued)

FOREIGN PATENT DOCUMENTS
WO 00/72905 A1 12/2000

OTHER PUBLICATIONS

Seleon GmbH, "THI® 20 Treatment with Nasal Insufflation", seleon@seleon.de.

(Continued)

*Primary Examiner* — Clinton T Ostrup
(74) *Attorney, Agent, or Firm* — Davis & Bujold, P.L.L.C.

(57) ABSTRACT

A nasal cannula, for supplying a respiratory gas to a patient, comprising: a pair of spaced apart supply lines which each have a head at one end thereof with a discharge opening therein. The opposite end of each supply line is connectable to a respiratory gas source. Each head is sized to be snugly received and retained within one of the nasal cavities of the patient while forming a sufficient leakage passage, between a portion of inwardly facing nasal cavity skin of a patient and a portion of an exterior surface of the head, to facilitate exhausting of any excess respiratory gas supplied to the patient through the leakage passage and also facilitate inhalation of any room air required in excess of the respiratory gas to be supplied to the patient. The invention also relates to a respiratory therapy system incorporating the nasal cannula, a method of treating a patient with sleep disorder by using the nasal cannula, a diagnostic tool for measuring nasal cavity pressure of a patient, and a method of using the diagnostic tool for measuring nasal cavity pressure of a patient.

17 Claims, 16 Drawing Sheets

U.S. PATENT DOCUMENTS

| | | | |
|---|---|---|---|
| 4,273,124 A * | 6/1981 | Zimmerman | 128/207.18 |
| 4,648,398 A * | 3/1987 | Agdanowski et al. | 128/207.18 |
| 4,660,555 A | 4/1987 | Payton | |
| 4,736,741 A | 4/1988 | Payton et al. | |
| 4,790,308 A * | 12/1988 | Weichselbaum | 128/207.18 |
| 5,105,807 A * | 4/1992 | Kahn et al. | 128/207.18 |
| 5,752,511 A * | 5/1998 | Simmons et al. | 128/207.18 |
| 5,775,335 A | 7/1998 | Seal | |
| 6,270,512 B1 * | 8/2001 | Rittmann | 128/207.18 |
| 7,007,694 B2 | 3/2006 | Aylsworth et al. | |
| 7,080,645 B2 | 7/2006 | Genger et al. | |
| 7,089,936 B2 | 8/2006 | Madaus et al. | |
| 2002/0017300 A1 | 2/2002 | Hickle et al. | |
| 2002/0100478 A1 | 8/2002 | Prime et al. | |
| 2002/0185131 A1 | 12/2002 | Madaus et al. | |
| 2004/0112382 A1 | 6/2004 | Schneider et al. | |
| 2004/0261797 A1 | 12/2004 | White et al. | |
| 2006/0037614 A1 | 2/2006 | Madaus et al. | |
| 2006/0272641 A1 | 12/2006 | Madaus et al. | |

OTHER PUBLICATIONS

McGinley, Brian M., Susheel P. Patil, Jason P. Kirkness, Phillip I. Smith, Alan R. Schwarta & Hartmut Schneider, "A Nasal Cannula Can Be Used to Treat Obstructive Sleep Apnea", *Am J Respir Crit Care Med*, vol. 176, Mar. 15, 2007, pp. 194-200.

\* cited by examiner

Fig. 15A
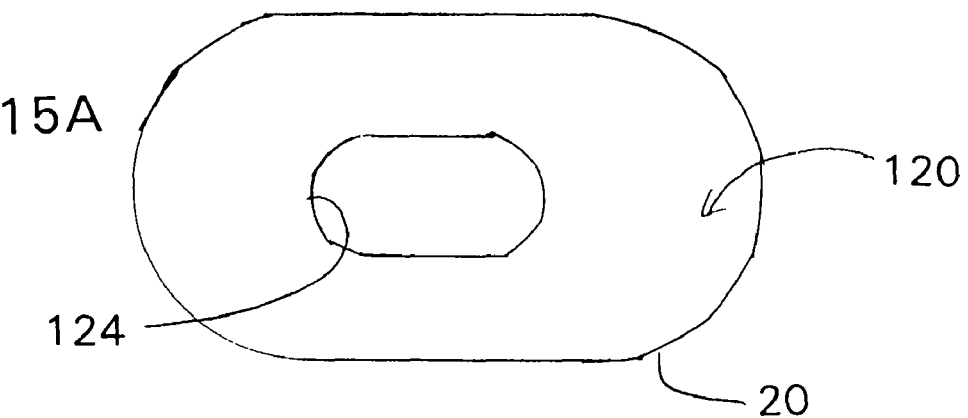
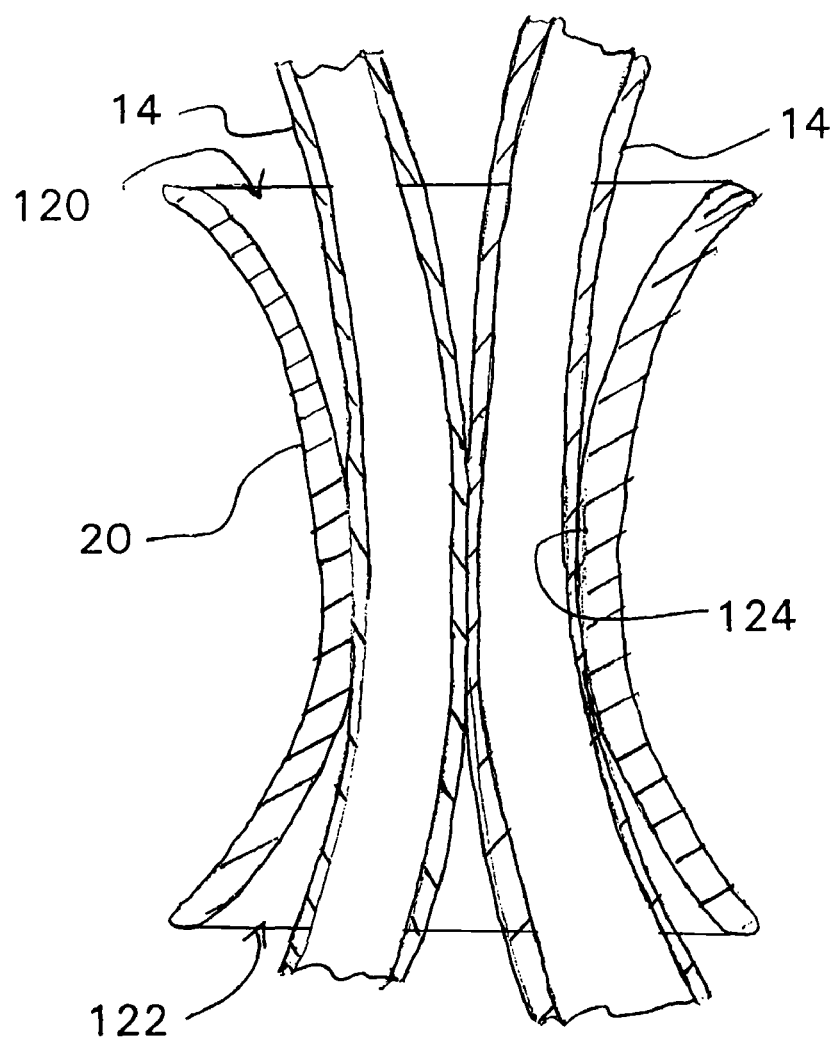
Fig. 15

RESPIRATORY THERAPY SYSTEM INCLUDING A NASAL CANNULA ASSEMBLY

This Application is a national stage completion of PCT/US2004/024291 filed Jul. 27, 2004 which is a continuation-in-part of provisional application No. 60/490,577 filed Jul. 28, 2003 which is a continuation-in-part of provisional application No. 60/528,008 filed Dec. 9, 2003.

FIELD OF THE INVENTION

The present invention relates in general to respiratory assistance equipment and, in particular, to a respiratory therapy system including a nasal cannula assembly for use in the administration of fluids such as oxygen into the nasal passages of a patient having respiratory ailments.

BACKGROUND OF THE INVENTION

A variety of flexible cannulas have been produced that are positioned to contact the nasal-labial area between the patient's upper lip and nostrils. Even though many of these cannulas were made of soft, flexible plastic, the wearer frequently encountered discomfort because a cannula is usually worn for a prolonged period of time. This results in continued contact of the cannula with the wearer's facial tissues, especially at the philtrum and around the unprotected nasal-labial area, thereby causing irritation and inflammation.

The structures of conventional cannula devices may be categorized into two general groups.

The first group utilizes a unitary member that includes a main tubular portion and a pair of tubular nasal prongs integrally connected to and in fluid communication with the main tubular portion. The main tubular portion has opposite ends which are connectable to flexible auxiliary oxygen supply tubes that are looped over the patient's ears and which themselves are in fluid communication with a pressurized source of oxygen. As is known, the nasal prongs are inserted into the nares of the wearer to deliver a low flow of oxygen to the patient's respiratory tract. The main tubular portion of these devices spans much if not all of the length of a wearer's upper lip. In so doing, the main tubular portion exerts contact pressure across much of the patient's upper lip. Under these circumstances, a patient usually begins to experience discomfort in a relatively short period of time even if the cannula itself and the auxiliary oxygen supply tubes connected thereto are designed to deliver relatively low flows of oxygen, i.e., they not particularly robust, stiff or heavy in weight. Examples of cannula devices and assemblies constructed in accordance with this first group may be found in, for example, U.S. Pat. Nos. 2,868,199; 3,643,660; 3,802,431; 4,106,505; 4,156,426; 5,400,776 and 5,794,619 and in published U.S. Patent Application Publications Nos. U.S. 2001/0031929 A1 and U.S. 2002/0112730 A1.

The second group involves a harness member that does not itself convey oxygen but which retains flexible auxiliary oxygen supply tubes in such a way that their discharge outlet ends define nasal prongs. However, the harness members of these devices also typically span all or most of the length of a patent's upper lip whereby the devices, even for light-duty gas delivery applications, produce the same patient discomfort problems as the cannula devices of the first group. Examples of cannula devices constructed according to the second group may be found in, for example, U.S. Pat. Nos. 2,931,358; 3,400,714; 4,278,082; 4,648,398; 4,790,308; 4,818,320 and 5,533,506.

Published United States Patent Application Publication No. U.S. 2002/0046755 A1 (the '755 publication) discloses various embodiments of nasal cannulas that fall into one or the other of the aforementioned groups, as well as other embodiments that are not as readily classifiable. However, none of the nasal cannulas disclosed in that publication describe a device that would be comfortable to a patient under the high flow conditions a patient would experience under positive airway pressure therapy, e.g., continuous positive airway pressure (CPAP) or bilevel positive airway pressure (BiPAP), that is often prescribed to patients suffering from Obstructive Sleep Apnea (OSA). For example, according to one embodiment of cannula taught in the '755 publication, a relatively narrow connector member that would rest against a patient's upper lip is integrally attached to the flexible auxiliary oxygen supply tubes whereby the ends of the tubes would function as nasal prongs that elastically engage the user's nasal septum inside of the nostrils. As used herein, the term "nasal septum," or simply "septum," means the wall that divides the nasal cavity into halves which terminate at the nostrils. At its front or anterior portion the septum is a firm but bendable structure made mostly of cartilage that is covered by skin. In order to deliver respiratory gas flow to a cannula that would be therapeutically desirable to maintain a typical adult patient's respiratory passageways open during OSA, for example, conventional auxiliary oxygen supply tubes must have an outer diameter of up to about ¼ inch (0.635 cm). Tubes of this caliber, when inserted short distances into the nostrils (as they must be so as not to harm the internal nasal tissues), would be quite obtrusive, stiff and uncomfortable to the user, especially when in elastic contact with the user's septum. Such discomfort would, in turn, detrimentally impact the patient's compliance with his or her prescribed positive airway pressure regime and, therefore, reduce the overall effectiveness of therapy.

U.S. Pat. Nos. 4,782,832; 5,042,478; 5,134,995; 5,269,296; 5,535,739; 5,687,715; 5,752,510; 6,431,172 and 6,478,026, well as published United States Patent Application Publication No. U.S. 2002/005935 A1, described nasal cannulas for positive airway pressure therapy. However, the cannula devices disclosed in these documents are quite large and cumbersome. Indeed, many are designed to cover and/or seal the patient's nostrils. Consequently, they too are not conducive to optimum patient therapy compliance.

An advantage exists, therefore, for respiratory therapy system including a nasal cannula assembly that is compact, lightweight and fabricated from highly flexible material. So constructed, the assembly would be comfortable for patients that undergo respiratory therapy involving the administration of pressurized respiratory gases for extended periods of time, including therapy involving the administration of pressurized respiratory gases at the high flow rates that are useful in positive airway pressure therapy.

SUMMARY OF THE INVENTION

The present invention provides a respiratory therapy system including a nasal cannular assembly adapted to contact the nasal-labial area of a patient's face. The cannula assembly comprises a nasal cannula, a pair of flexible auxiliary respiratory gas supply lines connected to the nasal cannula, a main respiratory gas supply line and, possibly a slip loop disposed about the auxiliary supply lines.

The nasal cannula is a unitary member desirably made of a highly flexible or pliable material. The cannula is molded so as to define a narrow central member and a pair of flexible supply arms integrally formed along opposite edges of the central member that are connectable to pair of auxiliary respiratory gas supply lines. The inner ends of the supply arms define a pair of spaced-apart hollow tubular extensions or prongs projecting in a slightly curved configuration from the central member. The tubular extensions are inserted into the nostrils of the wearer and their slightly curved configuration permits a positive guiding of the respiratory gas supply along the natural contours of the nasal passages into the pharynx.

The upper surface of the central member is preferably rounded in order to minimize the area of contact on the lower, outer surface of the nasal septum and to avoid any straight or sharp edges that would concentrate pressure against the septum. This, coupled with the inherent flexibility and short length of the central member, allows the cannula to lightly contact a small portion of the nasal-labial area of the patient.

In addition, the flexible supply arms of the cannula are designed such that when they are connected to the auxiliary respiratory gas supply lines and the cannula assembly is properly donned by the patient, the arms flex in such a way as to urge the auxiliary respiratory gas supply lines to pass under, rather than across or above, the patient's cheekbones. The advantage of this effect is that it avoids the discomfort that some patients experience when nasal cannula auxiliary respiratory gas supply lines contact the tissues of their cheekbone structures. Thus, when the nasal cannula assembly of the present invention is subjected to the pulling force of the auxiliary respiratory gas supply lines when the assembly is worn by a patient, it exerts minimal pressure against the patient's nasal-labial. In addition, it provides positive positioning of the tubular extensions within the nasal passages while spacing their surfaces from the interior walls of the nasal passages, including the septum. The result is a highly comfortable assembly that can be worn by a patient for long periods of time even under conditions of high gas flow rate whereby the patient is more likely to comply with and obtain the optimum benefits from his or her respiratory therapy regime.

Another object of the present invention is to increase resistance to the patient, upon exhalation, while not substantially increasing the breathing work of the patient during inhalation so that the breathing rate of the patient remains substantially at the same rate.

Still another object of the present invention is to introduce a sufficient amount of a treating or a respiratory gas, such as oxygen, medicine, etc. (all of which hereinafter are referred to as a "respiratory gas") into the nasal cavity of the patient in order to dilute or blow or drive off much of the carbon dioxide, in the process of being exhaled by the patient during an exhalation breath, and replace that blown or driven off carbon dioxide with the respiratory gas which can thereafter be readily inhaled by the patient during his/her subsequent inhalation breath.

Yet another object of the present invention is to provide a respiratory gas supply system which is readily retained within the nostrils of a patient while still being received therein so as to facilitate leakage between the inwardly facing nostril skin and the exterior surfaces of the nasal prongs to permit blowing or driving off some of the carbon dioxide contained within the exhalation breath of the patient.

A still further object of the present invention is to normally provide an excess quantity of the respiratory gas to the patient, at a constant flow rate, while allowing some of the excess respiratory gas to leak between the inwardly facing nostril skin and the exterior surfaces of the nasal prongs.

Another object of the present invention is to design a respiratory gas supply system which adequately heats and moisturizes the respiratory gas, prior to delivering the same to the patient, while also minimizing any condensation, along the supply conduit, of moisture contained in the respiratory gas and also reducing the noise generated by the respiratory gas supply system, to a decibel level approaching about 46 decibel, during delivery of the respiratory gas.

A further object of the present invention is to generate and maintain a sufficient back pressure in the patient, utilizing the respiratory gas supply system, so that the soft palate of the patient remain sufficiently inflated and are prevented from collapsing.

Still another object of the present invention is to provide a respiratory gas supply system which is able to sleep apnea.

The present invention relates to a nasal cannula for supplying a respiratory gas to a patient, the nasal cannula comprising: a pair of supply lines which each have a head at one end thereof with a discharge opening therein for discharging a respiratory gas, and the opposite end of each of the pair of supply lines being connectable to a respiratory gas source; wherein each head is sized to be snugly received and retained within one of the nasal cavities of the patient while forming a sufficient leakage passage, between a portion of inwardly facing nasal cavity skin of a patient and a portion of an exterior surface of the head, to facilitate exhausting of any excess respiratory gas supplied to the patient through the leakage passage and also facilitate inhalation of any room air required in excess of the respiratory gas to be supplied to the patient.

The present invention relates to a nasal cannula assembly for supplying a respiratory gas to a patient, the nasal cannula assembly comprising: a pair of supply lines which each have a head at one end thereof with a discharge opening therein for discharging a respiratory gas, and the opposite end of each of the pair of supply lines being connected to an auxiliary respiratory gas supply line; and a remote end of each of the auxiliary respiratory gas supply line is connected with a respiratory gas source for supplying a respiratory gas to a patient; wherein each head is sized to be snugly received and retained within one of the nasal cavities of the patient while forming a sufficient leakage passage, between a portion of inwardly facing nasal cavity skin of a patient and a portion of an exterior surface of the head, to facilitate exhausting of any excess respiratory gas supplied to the patient through the leakage passage and also facilitate inhalation of any room air required in excess of the respiratory gas to be supplied to the patient.

The present invention relates to a respiratory therapy system for supplying a respiratory gas to a patient via a nasal cannula, the respiratory therapy system comprising: a source of respiratory gas for supplying a respiratory gas to a patient; a nasal cannula connected to the source of respiratory gas for receiving the respiratory gas and supplying the respiratory gas to nostrils of a patient; the nasal cannula comprising: a pair of supply lines which each have a head at one end thereof with a discharge opening therein for discharging a respiratory gas, and the opposite end of each of the pair of supply lines being connected to an auxiliary respiratory gas supply line; and a remote end of each of the auxiliary respiratory gas supply line is connected with a respiratory gas source for supplying a respiratory gas to a patient; wherein each head is sized to be snugly received and retained within one of the nasal cavities of the patient while forming a sufficient leakage passage, between a portion of inwardly facing nasal cavity skin of a patient and a portion of an exterior surface of the head, to facilitate exhausting of any excess respiratory gas supplied to the patient through the leakage passage and also facilitate inhalation of any room air required in excess of the respiratory gas to be supplied to the patient.

The present invention relates to a method of treating a patient with sleep disorder with a respiratory gas, the method comprising the steps of: inserting prongs of a nasal cannula within respective nostrils of the patient; supplying a respiratory gas to the nasal cannula at a constant flow rate sufficient to form a back pressure within the breathing passageways of the patient, at least when the patient is exhaling; and allowing, at least during exhalation, a portion of the supplied respiratory gas to leak from the nostril between the prongs of the nasal cannula and inwardly facing skin of the nostril.

The present invention relates to a diagnostic tool for measuring nasal cavity pressure of a patient, the diagnostic tool comprising a the nasal cannula comprising: a pair of supply lines which each have a head at one end thereof with a discharge opening therein for discharging a respiratory gas, and the opposite end of each of the pair of supply lines being connectable to a respiratory gas source; each head being sized to be snugly received and retained within one of the nasal cavities of the patient while forming a sufficient leakage passage, between a portion of inwardly facing nasal cavity skin of a patient and a portion of an exterior surface of the head, to facilitate exhausting of any excess respiratory gas supplied to the patient through the leakage passage and also facilitate inhalation of any room air required in excess of the respiratory gas to be supplied to the patient; pressure sensing probe associated with each head; and each of the pressure sensing probe is coupled to supply a pressure reading to a pressure sensing device.

The present invention relates to a method of using a diagnostic tool for measuring nasal cavity pressure of a patient, the method comprising the steps of: permitting a patient to sleep; monitoring the sleeping patient with a diagnostic tool while a respiratory gas is supplied to a patient at a first flow rate; determining a pressure within the nasal cavity of the patient via a pressure sensing probe of the diagnostic tool; and adjusting the flow rate of the respiratory gas until an optimum respiratory gas flow rate is achieved which generates a desired back pressure within the breathing passages of the patient so that the patient uniformly breathes while sleeping.

As used in this patent application and in the appended claims, sleep apnea, obstructed sleep apnea, oxygen desaturation, and other related breathing interruptions, etc., all herein after referred to as "sleep disorder".

As used in this patent application and in the appended claims, the term "constant flow rate" means that the supply of the respiratory gas to the patient must be at a sufficient flow rate to be efficacious, e.g., generate a desired back pressure within the breathing passageways of the patient to facilitate breathing, not being excess so as to provide discomfort to the patient.

As used in this patent application and in the appended claims, the term "trough" means an opening, passageway, indentation or some other exterior surface irregularity such as, for example, a channel, a groove, a slot, a flute, or the like which facilitates leakage, in either flow direction, between the inwardly facing nasal cavity skin of a patient and the exterior surface of the head of the cannula.

As used in this patent application and in the appended claims, the term "supply line" means an arm, a conduit, a tube, a duct, a channel, or some other confined flow path for supplying a respiratory gas from a source to a patient.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent form the following description of preferred embodiments thereof shown, by way of example only, in the accompanying drawings where:

FIG. 15 is a diagrammatic cross sectional view of a slip loop to control tensioning of the pair of auxiliary respiratory gas supply lines; and FIG. 15A is a diagrammatic top plan view of the slip loop of FIG. 15.

DETAILED DESCRIPTION OF THE INVENTION

Figure 1:
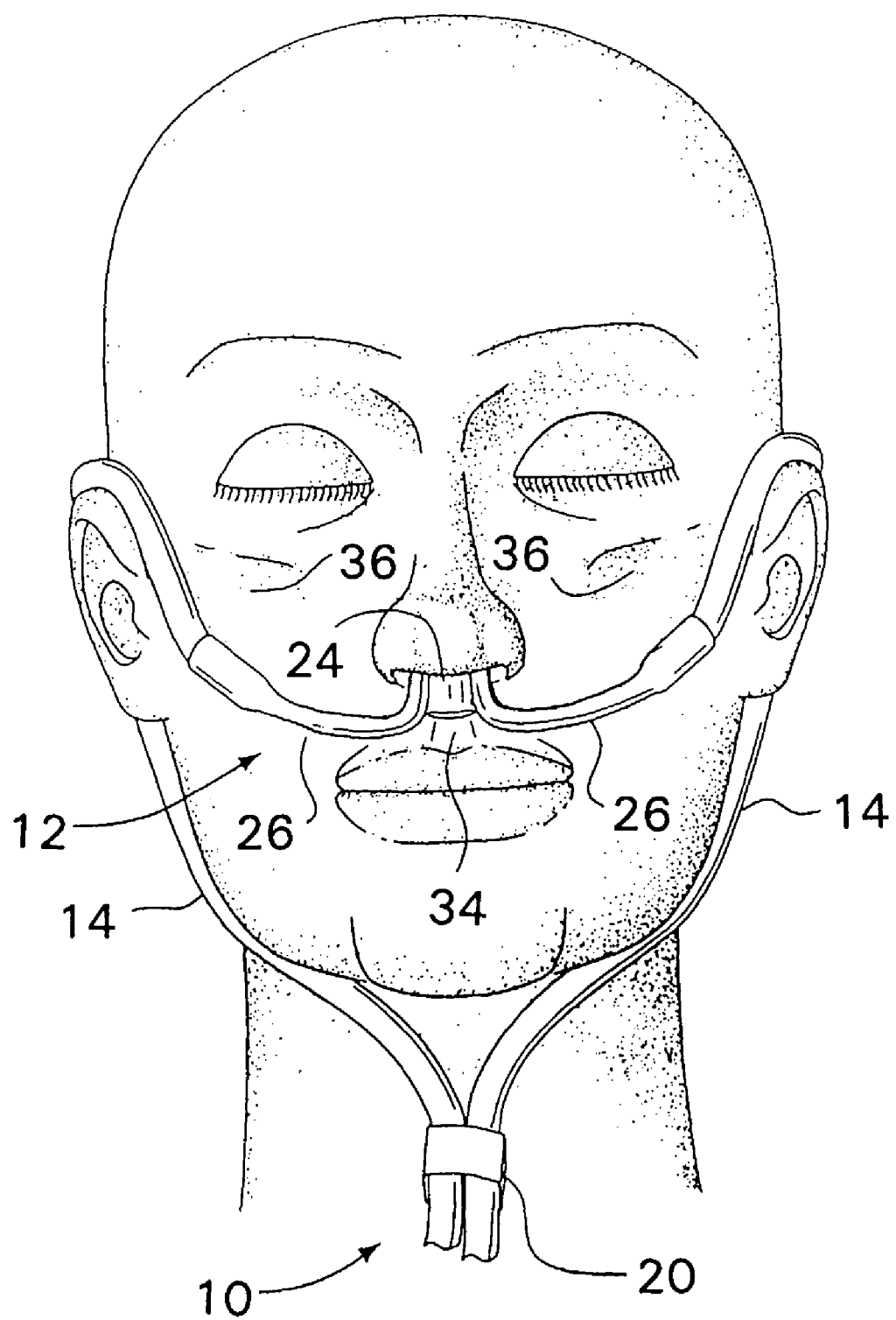
FIG. 1 is an enlarged elevational view of a portion of a cannula assembly according to the present invention in operative position on a patient.
Figure 2:
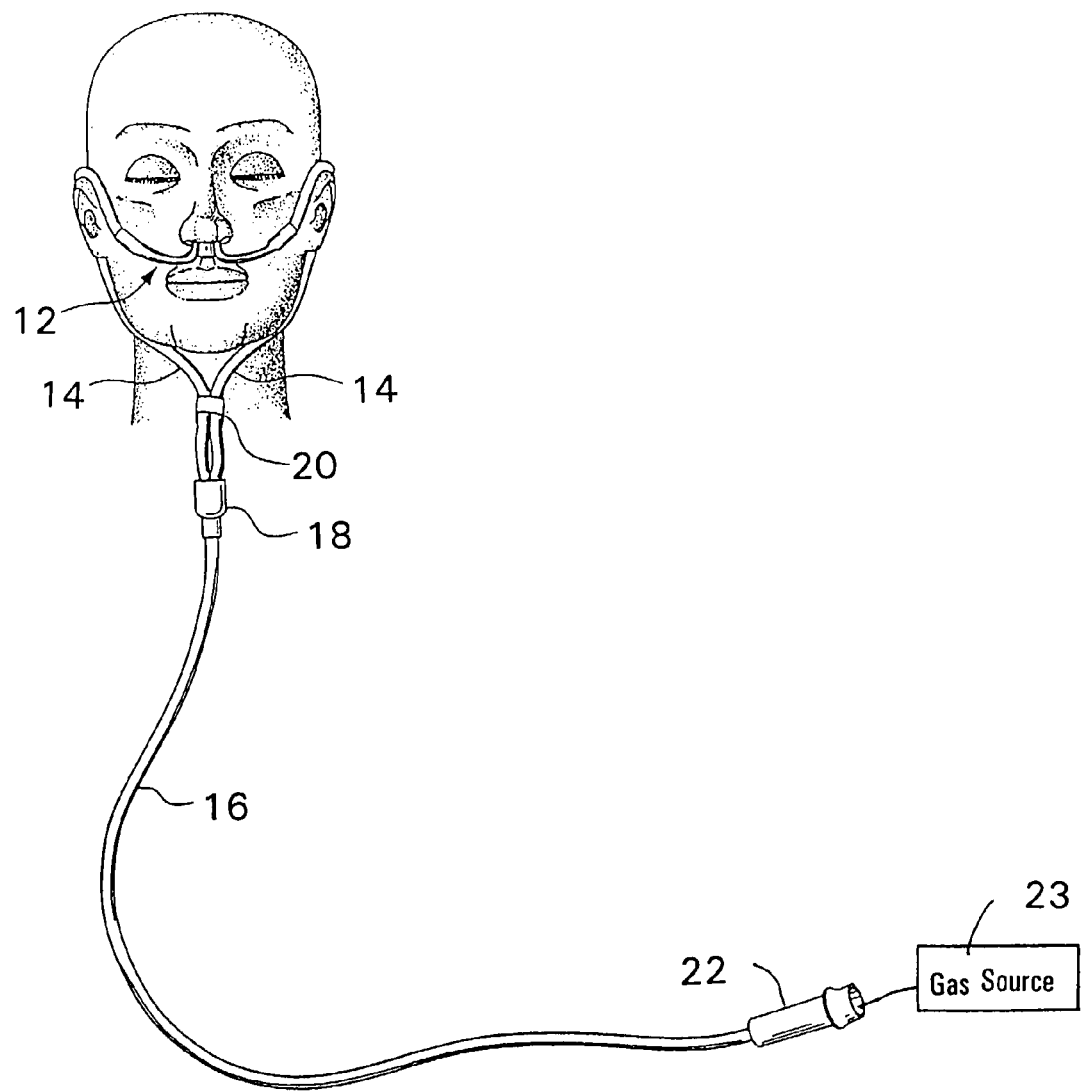
FIG. 2 is an elevational view of a complete cannula assembly according to the present invention in an operative position on a patient.

Referring to the drawings wherein like or similar references indicate like or similar elements throughout the several view, a nasal cannula assembly, according to the present invention, generally designated by reference numeral 10, is shown in FIGS. 1 and 2 in an operative position on a patient's face. The nasal cannula assembly 10 comprises a nasal cannula 12, a pair of auxiliary respiratory gas supply lines 14 connected to supply lines or arms 26 of the cannula (described below in further detail), a main respiratory gas supply line 16, a connector 18 for coupling each of the auxiliary lines 14 to the main respiratory gas supply line 16, an optional slip loop or line tightening member 20 disposed about auxiliary lines 14 for facilitating adjustment of the auxiliary lines about the patient's ears and head, and an end connector 22 for facilitating connection of a second end of the main respiratory gas supply line 16 to a pressurized respiratory or respiratory gas source 23. As described in greater detail below with reference to FIG. 6, the pressurized respiratory or respiratory gas source 23 comprises a compressor for delivering pressurized air (such as is commonly used in the treatment of OSA). Depending on a patient's therapeutic needs, a respiratory therapy system including the pressurized respiratory or respiratory gas source 23 may deliver heated and humidified respiratory gas to a patient.

Cannula 12 is generally a unitary member that may be fabricated by any suitable molding process such as, for example, by a dip molding process. Examples of dip molding processes for cannula formation include those disclosed in U.S. patent application Ser. Nos. 09/754,471 and 09/883,843 (both of which are entitled "Method to Produce Nasal and Oral Cannula Breathing Detection Devices") and the disclosures thereof are incorporated herein by reference in their entireties. The composition of cannula 12 is preferably a thermoplastic composition such as polyvinyl chloride, polyvinyl acetate, polyethylene, soft latex or other materials that are highly pliable or flexible.

Figure 3:
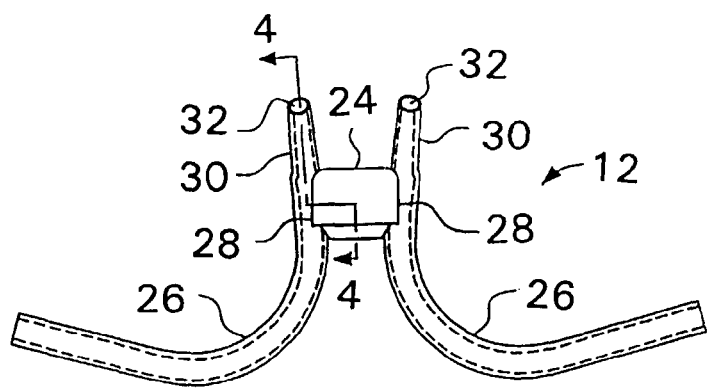
FIG. 3 is a rear elevational view of the cannula of the cannula assembly according to the present invention.
Figure 5:
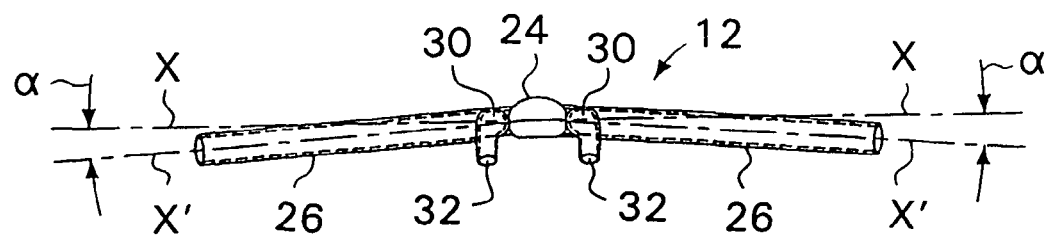
FIG. 5 is a top plan view of the cannula of FIG. 3.

As most clearly illustrated in FIGS. 1, 3 and 5, cannula 12 comprises a narrow or short-length central bridge member 24 which spaces apart a pair of substantially right angle flexible supply arms 26. The ridges of the supply arms 26 are integrally connected to the central bridge member 24 along opposite side end edges 28 thereof (as shown in FIG. 3) and the second ends of the supply arms 26 are respectively connectable to one of the auxiliary respiratory gas supply lines 14 (as shown in FIGS. 1 and 2). The connection between supply arms 26 of cannula 12 and auxiliary respiratory gas supply lines 14 may be effectuated by any suitable method or means and the connection may be either releasable or permanent. For example, according to a presently preferred embodiment, the supply arms 26 are intimately received within the auxiliary respiratory gas supply lines 14 and their connections may be maintained by friction fit, a solvent, adhesive bonding, ultrasonic welding, etc.

Figure 4:
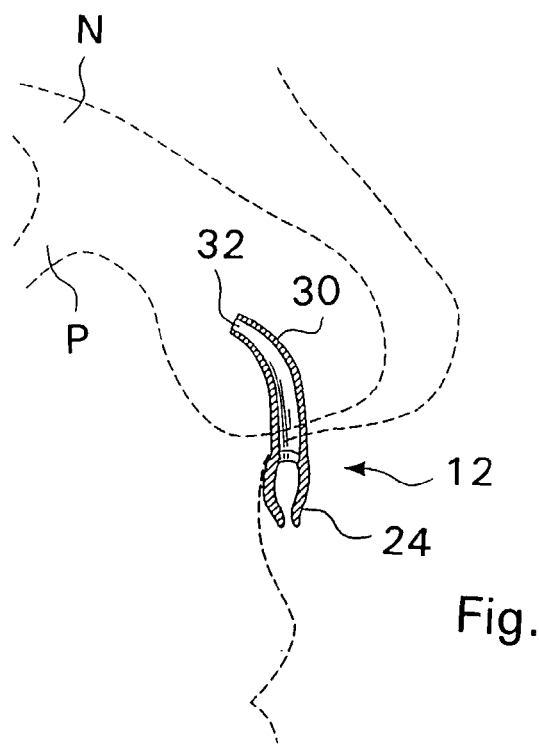
FIG. 4 is an enlarged cross-sectional view taken along line 4-4 of FIG. 3 showing the relative position of the cannula of FIG. 3 when secured to a patient with its extensions inserted into the patent's nasal cavity.

As shown in FIGS. 4 and 5, a nozzle or hollow tubular extension 30 is integrally formed with and project upwardly from the ridge of each of the supply arms 26. Each tubular extension 30 preferably assumes a slightly curved configuration, corresponding substantially to that of an anterior region of a patient's nasal cavity, and terminates in a respiratory gas discharge outlet 32. For optimum patient comfort, each tubular extension 30 preferably tapers upwardly from the top of the central bridge member 24 to the discharge outlets 32. In operation, each tubular extension 30 is inserted into one of the nostrils of the patient so as to extend into the nasal cavity N. The curved configuration of the tubular extensions 30 permits a positive guiding of the respiratory gas supply along the natural contours of the nasal passages into the pharynx P rather than toward the upper reaches of the nasal cavity where the respiratory gas may cause pressure and potentially irritate the patient. In addition, there are no sharp edges along or at the tip of the tubular extensions 30 which could irritate the nasal passage due to the movements induced by patient breathing and the soft, flexible material of the cannula permits the extensions to easily conform to the contours of the nasal cavity N.

Unlike some conventional nasal cannulas that possess structure which spans most, if not all of a patient's upper lip, the central bridge member 24 of cannula 12 is quite narrow and has a relatively short axial length. Indeed, it is configured to span substantially no more than the width of the patient's philtrum 34 (FIG. 1). As a result, a minimal area of the front surface of the patient's upper lip is in continuous contact with a rear surface of the central bridge member 24 and the cannula 12 during use of the cannula. Additionally, as shown in FIG. 4, the upper surface of central bridge member 24 is preferably rounded in order to minimize the area of contact on the lower, outer surface of the nasal septum and to avoid any sharp or straight edges that may concentrate pressure thereagainst. Thus, the combination of these features causes the cannula 12 to lightly contact a small portion of the nasal-labial of the patient, thereby enhancing both the comfort to a patient who must wear a nasal cannula 12 for prolonged periods of time and the patient's willingness to comply with his/her CPAP therapy program.

FIGS. 1 and 2 illustrate the preferred manner in which the cannula assembly 10 is to be worn by a patient. The cannula 12 generally rests across the patient's nasal-labial area while the flexible auxiliary respiratory gas supply lines 14 initially extend across the patient's face, over and behind the patient's ears, down the haw areas and are brought together under the chin of the patient. The line tightening member 20, which is of sufficient size to encompass both of the auxiliary supply lines 14, may then be adjusted along the length of the auxiliary supply lines 14 so that the cannula 12 will remain firmly in place without the auxiliary supply lines 14 being uncomfortably taut on the patient.

As depicted in FIG. 5, the central bridge member 24 of cannula 12, according to one construction, defines a horizontal plane X. Each of the supply arms 26 lie on one side of the horizontal plane X and lie in a respective horizontal plane X' that forms an acute angle $\alpha$ relative to the horizontal plane X of the central bridge member 24. Disposing the supply arms 26 at an angle $\alpha$, with respect to the horizontal plane X of the central bridge member 24, serves to minimize the amount of tension and/or force that must be applied to the auxiliary respiratory gas supply lines 14 to maintain the cannula 12 in position against the patient's nasal-labial.

Additionally, as shown in FIG. 3, the opposite end of each of the supply arms 26 initially extends away from the ridge and the central bridge member 24 and then bends and turns outwardly away from one another to the second end in a gently curved configuration having a radius of curvature of about 0.4 inch to about 0.8 inch depending on the facial characteristics and head size of the patient that will use the device, e.g., child or adult. Although supply arms 26 are highly flexible and yieldable they nevertheless possess sufficient resilience or stiffness to impart a desirable configuration to the auxiliary supply lines 14 which further enhances the patient's comfort. That is, the curved supply arms 26 function to urge the auxiliary respiratory gas supply lines 14 to pass beneath and around, rather than across or over, the patient's cheekbone areas 36 (FIG. 1). This arrangement advantageously avoids the discomfort that some patients experience when the nasal cannula auxiliary respiratory gas supply lines contact their cheekbone areas 36. Thus, when the nasal cannula assembly 10 of the present invention is subjected to the pulling force of the auxiliary respiratory gas supply lines 14 when the assembly is worn by a patient (which pulling force is greater for larger caliber and stiffer auxiliary respiratory gas supply lines that are designed to deliver high respiratory gas flows), it exerts minimal pressure against both the patient's nasal-labial 34 and cheekbone areas 36.

As mentioned above, the nasal cannula assembly 10 is beneficial whether it is used to convey respiratory gases under low flow rates, such as might be administered for oxygen assistance therapy, or high flow rates of at least about 28 liters per minute, as might be required for positive airway pressure administration for treatment of OSA. In any event, the dimensions of the main respiratory gas supply line 16, the auxiliary respiratory gas supply lines 14 and the cannula supply arms 26 will be optimized to provide minimum bulk and weight, minimal pressure drop, maximum flow and minimum turbulence and noise generation. In addition, it will be understood that the nasal cannula 12 may be molded to any dimensions suitable to accommodate the particular physical facial characteristics and sizes of a patent ranging in size from very small children or infants to very large adults. The result is a highly comfortable assembly that can be worn by a patient for long periods of time even under conditions of high gas flow rates whereby the patient is more likely to comply with and obtain the optimum benefits of his or her respiratory therapy regime.

Figure 6:
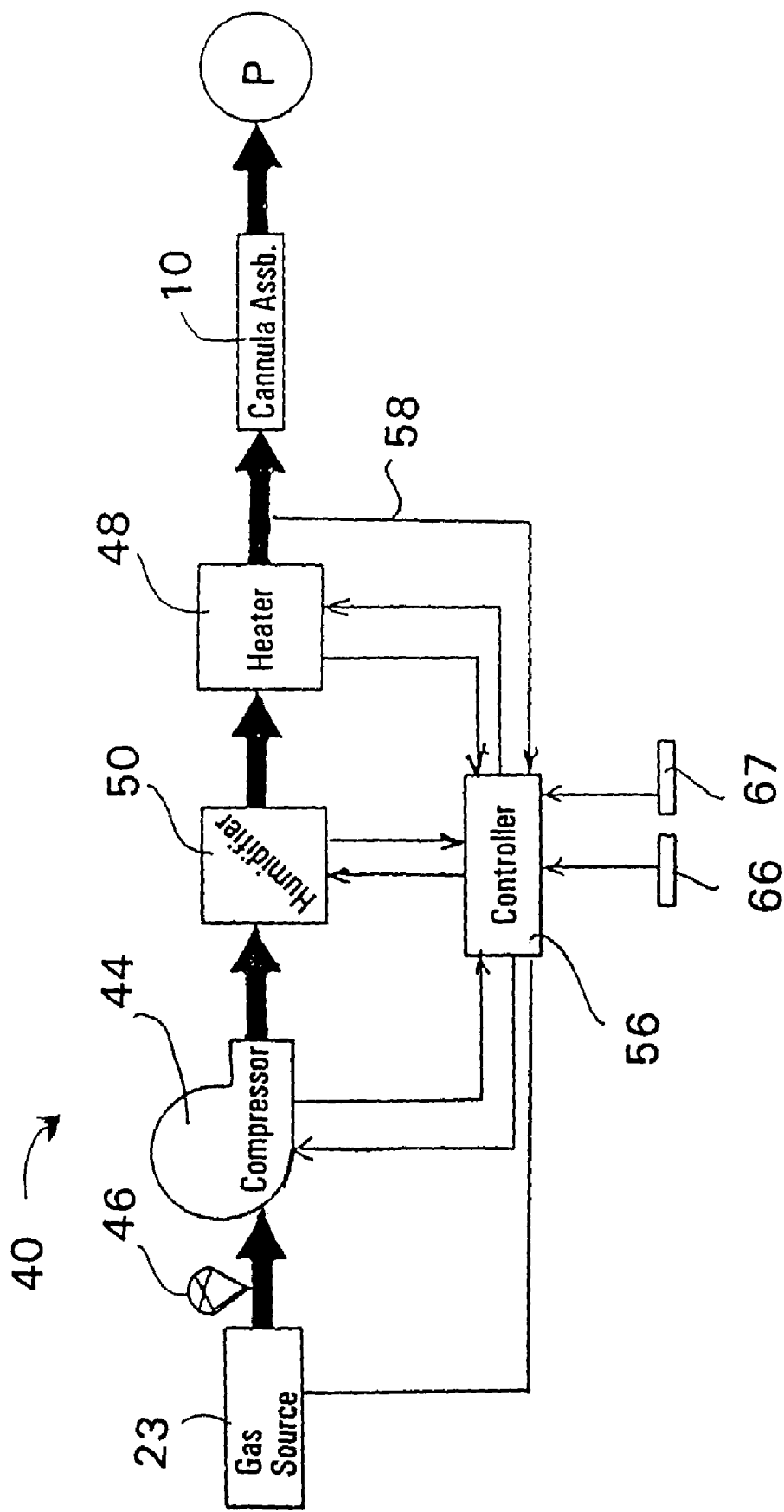
FIG. 6 is a block diagram of a respiratory therapy system including a nasal cannula assembly according to the present invention.

FIG. 6 illustrates, in general, a respiratory therapy system 40 including a pressurized respiratory or respiratory gas source 23 for supplying the respiratory gas to the system 40 and the patient P, and a nasal cannula assembly 10 according to the present invention. The respiratory therapy system 40, described in further detail below, can be generally defined as an open system providing a high flow of a respiratory gas to the patient P. An open system is generally open to the effects of ambient air pressure. As is readily apparent to one skilled in the art, this occurs adjacent the discharge opening 32 of the nasal cannula assembly 10 where the respiratory gas flow is introduced into the nostrils of the patient's nose and a portion of the respiratory gas along with a portion of the exhaled gases of the patient, is allowed to leak out through the nostril/tubular extension interface.

In contrast to the open respiratory therapy system 40 of present invention, the previously known sleep apnea gas delivery systems are, in general, closed systems which provide a respiratory gas at a specified higher pressure relative to the ambient air pressure. In such closed systems, a face mask is sealed over the mouth and/or nose of the patient P, thus creating the closed pressure system. A closed gas delivery system may generate pressures in the range of 4 to 20 cm $H_2O$ in the patient's respiratory passages to maintain open airways. The sealed mask is, of course, worn by the patient while he/she is sleeping. However, the sealed mask and the pressure developed thereby with the delivered respiratory gas are particularly uncomfortable to the patient and the treatment is often prematurely abandoned by the patient after several sessions due to a variety of reasons, e.g., discomfort of the mask, etc.

In many cases of sleep apnea, the burden and effect of such closed systems is not necessary. The open respiratory therapy system 40 of the present invention overcomes the above noted drawbacks of known closed therapy systems. The above described nasal cannula assembly 10 is substantially more comfortable for the patient to wear then the masks used in known sleep apnea treating systems. Thus, the patient is less apt to remove the mask and forego the therapy due to discomfort. The delivery of a high flow of respiratory gas to the patient's airways ensures that there is an abundance of the respiratory gas available to the patient which is delivered at 3 to 15 cm of $H_2O$ pressure.

Figure 7:
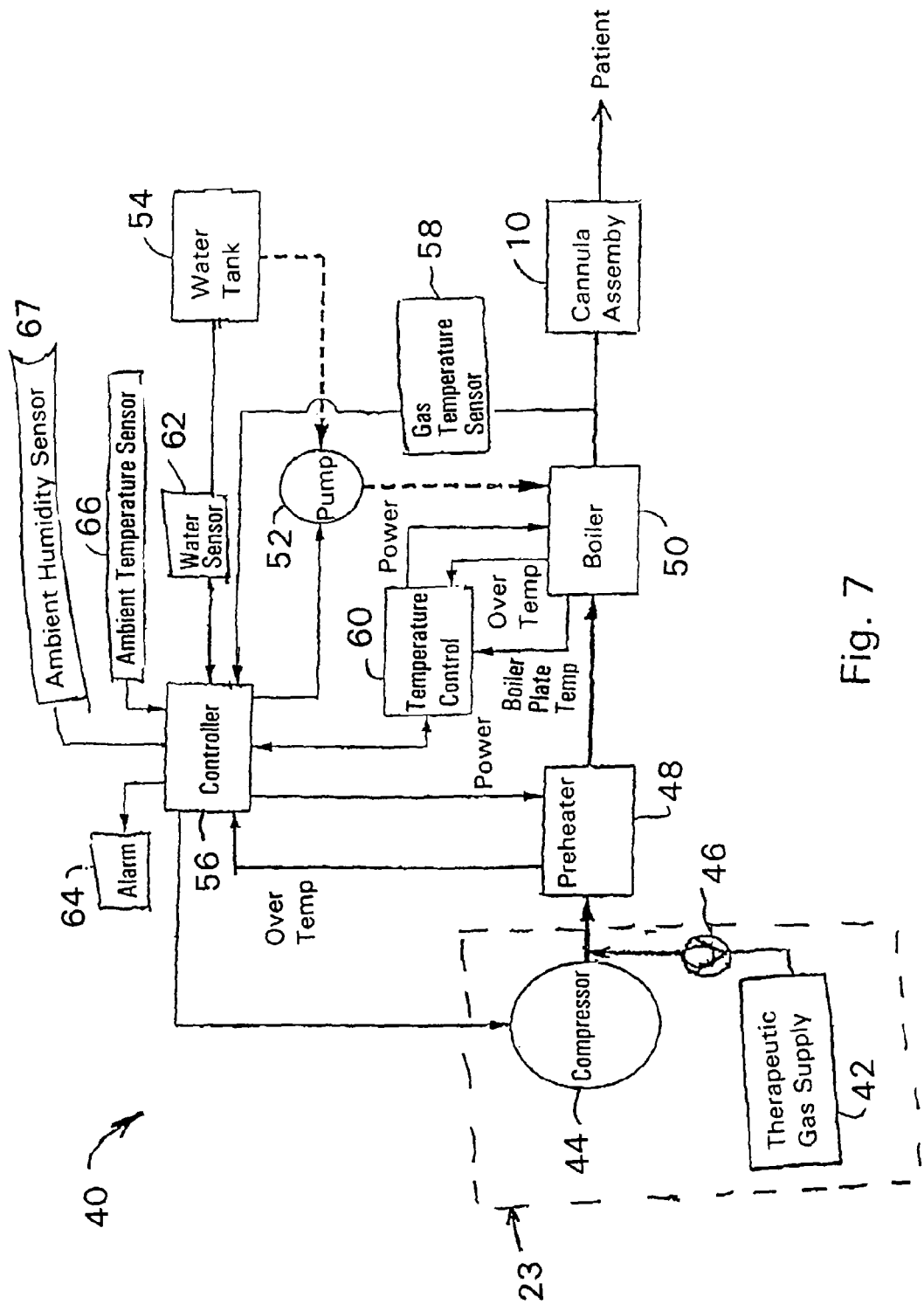
FIG. 7 is a diagrammatic view of another embodiment of the respiratory therapy system.

In general, as shown by the heavy black arrows of FIG. 6 as well as in FIG. 7, the respiratory therapy system 40 of the present invention supplies a respiratory gas from a source 23 to an initial gas flow developing/measuring mechanism 44 for imparting a desired high flow rate of the respiratory gas through a remainder of the respiratory therapy system 40 to the nasal cannula assembly 10 and into the patient's upper respiratory system. The high flow rate permits the patient's lungs to freely draw in the respiratory gas, and the high flow rate of respiratory gas provides a rich, abundant source of the respiratory gas without the need for developing a significant over pressure in the patient's lungs by using a mask to cover the patient's mouth and nose. The flow developing/measuring mechanism 44, for developing the desired respiratory gas flow rate, can be, for example, a compressor, a fan, a pump, a blower or some other conventional device which is well known in the art. The flow developing/measuring mechanism 44 typically will supply the respiratory gas at a rate of from about 26 to about 60 liters per minute, preferably about 50 liters per minute, at a pressure of from between 3 and 15 cm of $H_2O$.

The respiratory gas generally is conditioned prior to delivery of the same to the patient. Generally a humidifier 50 is provided for conditioning the respiratory gas prior to delivery to the patient. The respiratory gas is typically warmed and humidified in order to minimize and/or avoid patient discomfort and possibly harm to the internal tissues of the patient's nasal cavity. In particular, respiratory gas supplied at the above described flow rates should be maintained at a relative humidity of about 70 percent and 100 percent and more preferably at a relative humidity of about 80 percent. Additionally, the temperature of the supplied gas should be within the range of about 81° F. (27.2° C.) and about 90° F. (32.2° C.) and more preferably at a temperature of about 86° F. (30.0° C.).

High flow conditions may also tend to create noise and turbulence in the auxiliary gas supply lines 14 and/or the supply arms 26 which may cause annoyance and/or discomfort to the patient and may be detrimental to the patient's long term use of the system. In order to minimize noise and turbulence, the components of the nasal cannula assembly 10, the auxiliary respiratory gas supply lines 14 and the main respiratory gas supply line 16 typically have an inner diameter of about 0.173 or 3/16 inch (0.068 cm) and an outer diameter of about 0.225 or 7/32 inch (0.088 cm), although other sizes are also contemplated and would be readily apparent to those skilled in the art. It is also possible to utilize ribbon supply conduit as long as the respiratory gas supply lines are sufficiently sized to satisfy the gas delivery conditions and prevent or minimize kinking thereof.

In the case of a specially prepared respiratory gas, a check valve or some other suitable supply gas metering device 46 is preferably provided, as part of the respiratory gas source 42, to conserve use of the respiratory gas. The respiratory gas is thus supplied via the metering device 46 to the flow developing/measuring mechanism 44. The flow developing/measuring mechanism 44 typically supplies the respiratory gas to the humidifier 50, for adequately humidifying the respiratory gas, and then to the heater 47, for adequately heating the respiratory gas, before finally supplying the same via the nasal cannula assembly 10 to the patient P.

A controller 56 is used to control the flow parameters of the respiratory therapy system 40, e.g., monitor the desired flow, as selected by the user, or as required by the ramp or re-ramp functions. The controller 56 provides adjustment for varying the respiratory gas flow rate from about 26 to 60 liters per minute, preferably about 50 liters per minute, over a period of from about 5 minutes to 30 minutes, to enable the patient to acclimate to the desired flow rate (ramp function). This ramp function can be used for both initial cold startups and hot interrupted sleep starts.

Additionally, the controller 56 continuously monitors the respiratory gas temperature and provides an input to the humidifier 50 and the heater 47 to control individually both the humidity and/or temperature of the supplied respiratory gas. The controller 56 also monitors and provides control of the temperature throughout the ramp functions so as to maximize patient comfort. The controller 56 is provided with control logic circuits to monitor and control these various aspects of the respiratory therapy system 40 and as such control logic circuits are conventional and well known in the art, a further detail discussion concerning the same is provided.

A number of other devices may also be provided to supply different inputs to the controller 56. For example, an ambient temperature sensor 66 may supply the ambient temperature to the controller 56 to optimize the temperature of the respiratory gas relative to the patient's ambient temperature surroundings. Also, the respiratory therapy system 40 may include an ambient humidity sensor 67 for sensing the ambient humidity to assist with a more effective control of the humidity of the respiratory gas leaving the humidifier 50.

Figure 8:
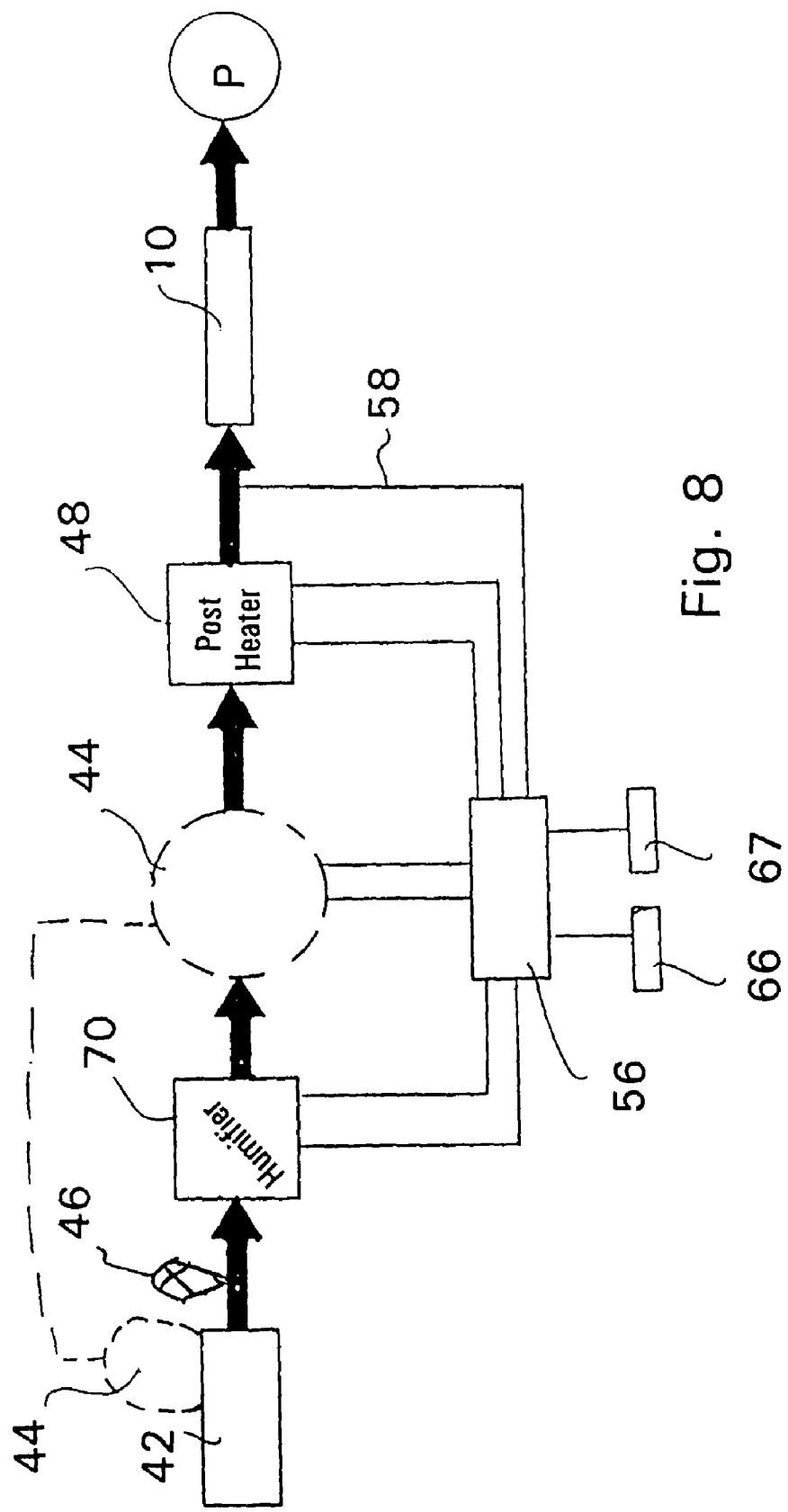
FIG. 8 is a block diagram of another embodiment of a respiratory therapy system including a nasal cannula assembly according to the present invention.

In a still further embodiment of the present invention, as shown in FIG. 8, the respiratory therapy system 40 may provide the respiratory gas, either before or after passing through 60 liters per minute, preferably about 50 liters per minute, a flow developing/measuring mechanism 44, through a pass over humidifier 70, or some other type of humidifier known in the art provided with variable heat control to more efficiently manage humidification and increase water vapor in the respiratory gas. The humidified respiratory gas is then conveyed to a heater (e.g., a post heater) 48 and subsequently supplied to the nasal cannula assembly 10 for delivery to the patient P. Again, as discussed above, the controller 56 is used to monitor and control the system components, namely, the flow developing/measuring mechanism 44, the humidifier 70 and the heater (e.g., a post heater) 48 to adequately control the temperature and humidity of the respiratory gas before delivery to the patient. A temperature measurement sensor 58 may be provided in the respiratory therapy system 40, after the heater (e.g., a post heater) 48, and the ambient room temperature sensor 66 and the ambient room humidity sensor 67 may provide the controller 56 with inputs to assist with ensuring that the respiratory gas is controlled at a desired temperature and humidity level prior to delivery to the patient P.

Preferably the respiratory gas, once being sufficiently heated and humidified by the respiratory therapy system 40 just prior to delivery to the patient, typically is delivered at a relative humidity of between 70 and 100 percent and more preferably a relative humidity of about 85 percent.

With respect to heating of the respiratory gas, a post heating arrangement is preferred as it heats up and cools down relatively quickly thereby facilitating more accurate control of the temperature of the respiratory gas being supplied to the patient.

Figure 9A:
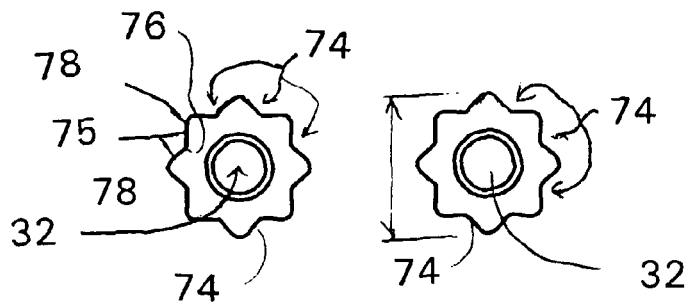
FIG. 9A is a diagrammatic view of the nasal cannula of FIG. 9 in the direction of section line 9A-9A of FIG. 9.
Figure 9:
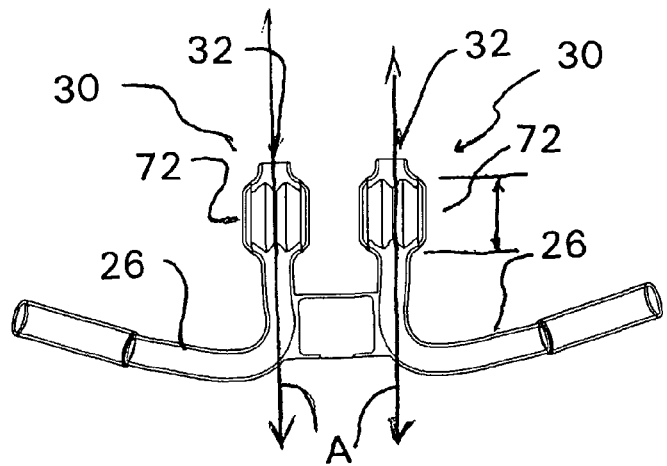
FIG. 9 is a front elevational view of a variation of the nasal cannula.
Figure 9B:
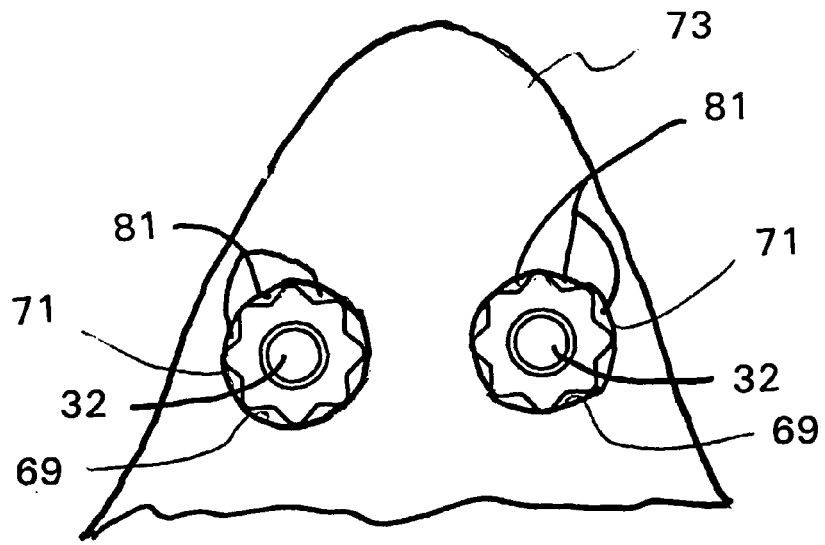
FIG. 9B is a diagrammatic front view showing the two heads of the nasal cannula received within the nostrils of a patient to define a plurality of leakage passages therebetween.
Figure 9C:
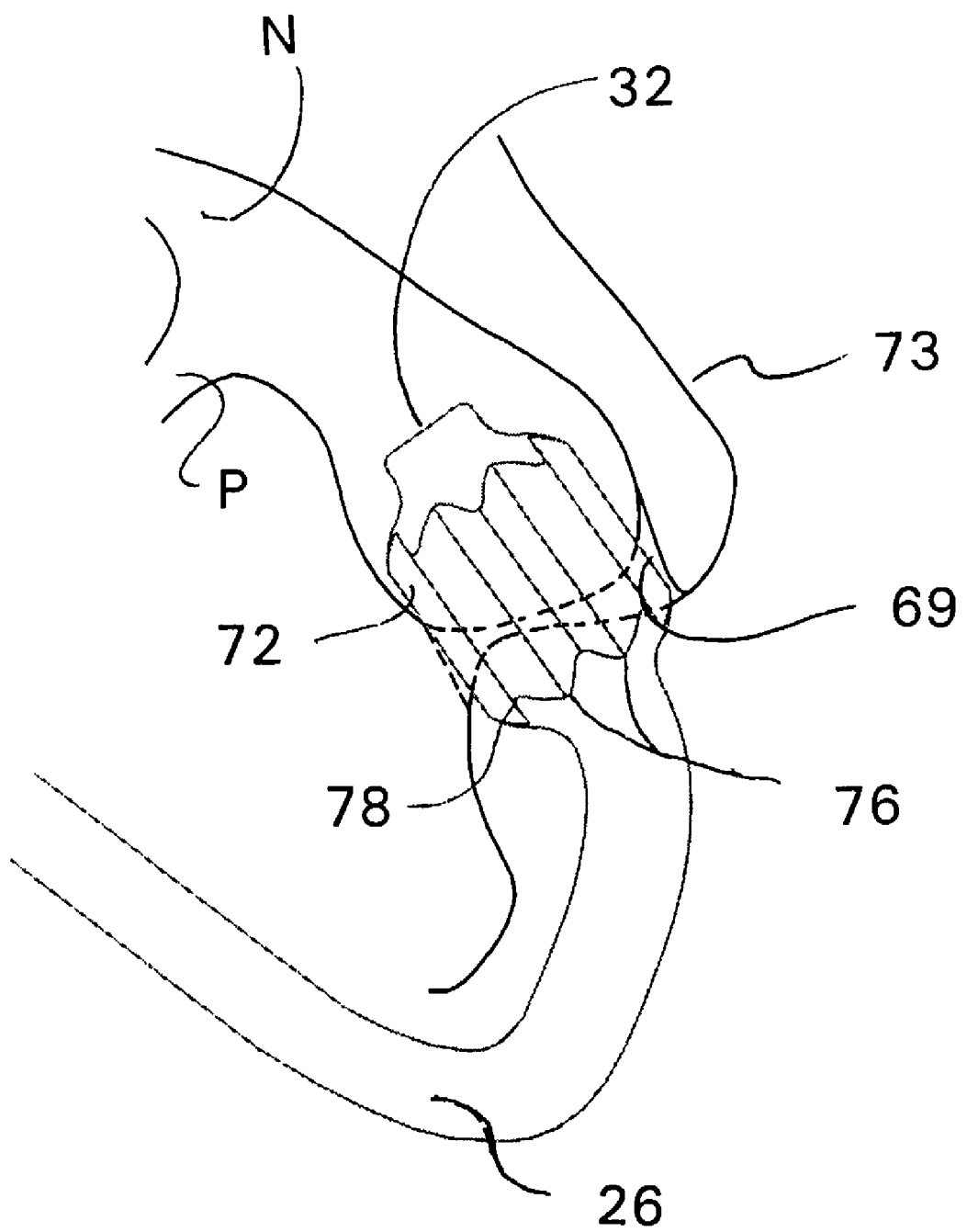
FIG. 9C is a diagrammatic side view of FIG. 9B showing the one of the two heads of the nasal cannula received within the nostrils of a patient.

With reference to FIGS. 9-9C, a further variation of the invention will now be described. As this embodiment is quite similar to the previous embodiment, only the differences between this embodiment and the previous embodiment will be discussed in detail. According to the embodiment, the prong end of each supply arm 26 includes an enlarged head 72 which contains the respiratory gas discharge outlet 32. The head 72 preferably has an elliptical transverse cross sectional shape (see FIGS. 10-10B) which facilitates both insertion and removal of the head 72 as well as retention thereof within the nostril of the patient. The maximum diameter of the elliptically shaped head may be slightly compressed as the head 72 is received within in the respective nostril and such slight compression of the head 72 leads to improved retention of the head 72 within the nostril without any perceived discomfort to the patient. Alternatively, the diameter of the head 72 may be substantially cylindrical in shape as is shown in FIGS. 7-9C. At least one and preferably a plurality of equally spaced apart elongate channels, grooves, slots, troughs or flutes 74 are formed in the exterior surface of the head 72. Each one of these elongate channels, grooves, slots, troughs or flutes 74 extends substantially parallel to, but is spaced from, a longitudinal axis A of the tubular extension 30 to facilitate exhausting of any excess supplied respiratory gas from the nasal cavity as well as permitting inhalation by the patient of any required additional air needed by a patient during inhalation. Each elongate channel, groove, slot, trough or flute 74 generally is defined by a pair of adjacent side surfaces 75, diverging from a common elongate valley 76, toward the pair of adjacent elongate ridges 78. In the first version of the head 72 (e.g., the larger model) shown in FIGS. 9-9B, the head 72 has a maximum outer diameter of between about 0.50 of an inch (1.3 cm) and about 0.70 of an inch (1.8 cm), preferably about 0.60 of an inch (1.5 cm) and has an axial length of between about 0.5 of an inch (1.3 cm) and about 0.60 of an inch (1.5 cm), preferably about 0.55 of an inch (1.4 cm) so that the head 72 is readily received and retained within a nostril 71 of a patient having a relatively large nostril (see FIGS. 9B and 9C). According to this embodiment, the enlarged head 72 has eight elongate channels, grooves, slots, troughs or flutes 74 equally spaced about the circumference of the head 72. Each valley 76 has a depth of between about 0.03 of an inch (0.08 cm) and about 0.06 of an inch (0.15 cm), preferably about 0.05 of an inch (0.13 cm).

Figure 10A:
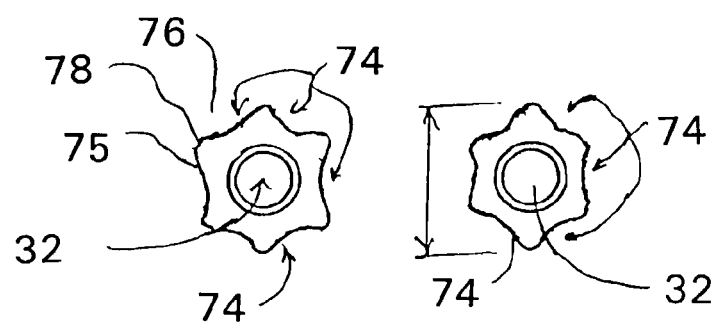
FIG. 10A is a diagrammatic view of the nasal cannula of FIG. 10 in the direction of section line 10A-10A of FIG. 10.
Figure 10:
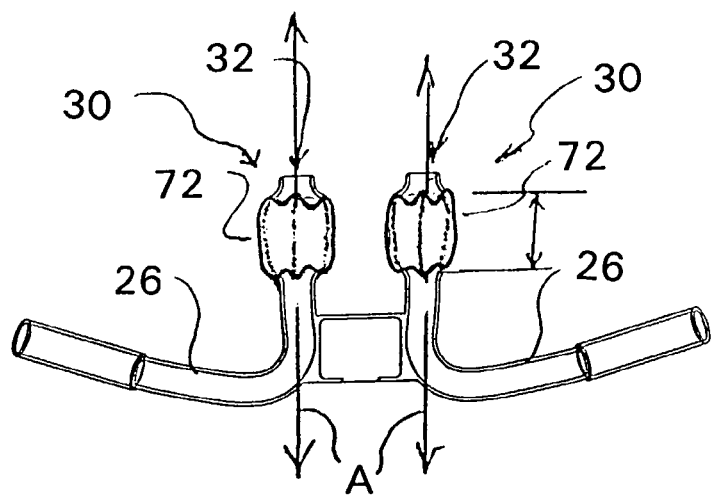
FIG. 10 is a front elevational view of another variation of the nasal cannula.
Figure 10B:
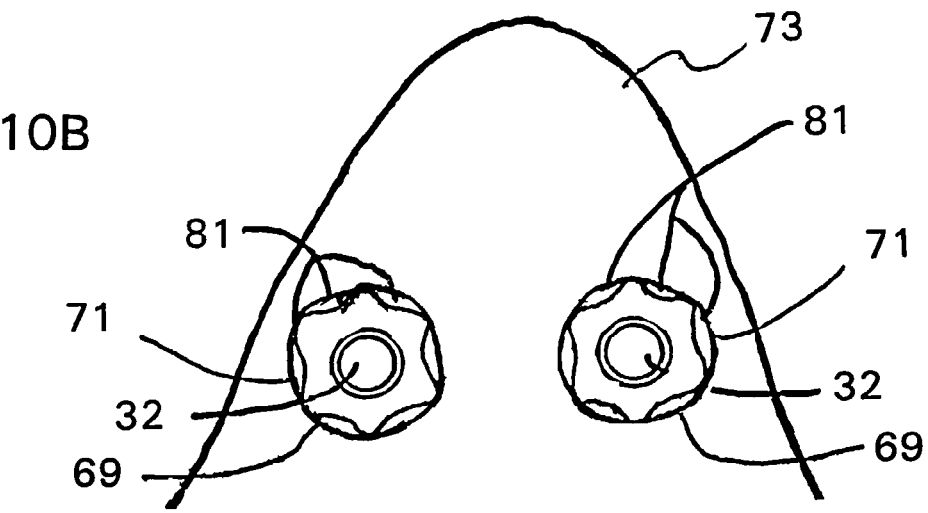
FIG. 10B is a diagrammatic view showing the two heads of the nasal cannula received within the nostrils of a patient to define a plurality of leakage passages therebetween.

According to a second version of shown in FIGS. 10-10B, e.g., a "smaller" version of the enlarged head 72, the head 72 has a maximum outer diameter of between about 0.345 of an inch (0.88 cm) and about 0.375 of an inch (0.95 cm), preferably about 0.355 of an inch (0.90 cm) and has an axial length of between about 0.30 of an inch (0.76 cm) and about 0.375 of an inch (0.95 cm), preferably about 0.35 of an inch (0.9 cm) so that the head 72 is readily received within a nostril 71 of a patient having relatively a smaller sized nostril (see FIG. 10B). According to this embodiment, the enlarged head 72 has six elongate channels, grooves, slots, troughs or flutes 74 equally spaced about the circumference of the head 72. Each valley 76 has a depth of between about 0.015 of an inch (0.04 cm) and about 0.035 of an inch (0.09 cm), preferably about 0.025 of an inch (0.06 cm).

It is to be appreciate to those skilled in this art that numerous variations concerning the number, the shape, the depth, the width, the size, the cross sectional leakage area, etc., of the elongate channels, grooves, slots, troughs or flutes 74 and leakage passageways 81 would be readily apparent to those skilled in the art depending upon the particular application. In view of this, a further detail description concerning such variations and/or modifications of the enlarged head 72, the side surfaces 75, the valleys 76, the elongate ridges 78 and/or the leakage passageway 81 is not provided herein but such numerous variations are considered to be within the spirit and scope of the present invention.

As the ridge of the nasal cannula 12 is received within the respective nostrils 71 of a nose 73 of the patient (see FIGS. 9B, 9C and 10B), the elongate valleys 76 of the nasal cannula 12 have a diameter which are sized to be slightly smaller than the perimeter opening of the nostril 71 of the patient so that a plurality of circumferentially spaced leakage passageways 81 are formed. Each one of the leakage passageways 81 is formed and defined by the pair of adjacent side surfaces 75, diverging from a common elongate valley 76 toward the pair of adjacent elongate ridges 78, and the inwardly facing skin tissue 69 of the nostril 71. For the large head 72 (see FIGS. 9-9B), the adjacent side surfaces 75, diverging from a common elongate valley 76, and the inwardly facing skin tissue 69 of the nostril 71 together define a cross sectional open area or leakage passageway 81 of between about 0.0045 square inches (0.029 cm$^2$) and 0.0055 square inches (0.035 cm$^2$), and preferably define a cross sectional open area or leakage passageway 81 of about 0.005 square inches (0.032 cm$^2$). For the smaller head 72 (see FIGS. 10-10B), the adjacent side surfaces 75, diverging from a common elongate valley 76, and the inwardly facing skin tissue of the nostril 71 together define a cross sectional open area or leakage passageway 81 of between about 0.002 square inches (0.013 cm$^2$) and 0.003 square inches (0.019 cm$^2$), and preferably define a cross sectional open area or leakage passageway 81 of about 0.0025 square inches (0.016 cm$^2$).

The head 72 is sized to facilitate retention of the nasal cannula 12 within a nostril 71 of a patient while the leakage passageways 81 prevent a fluid tight seal from being formed, between the exterior surface of the enlarged head 72 of the nasal cannula 12 and the inwardly facing skin tissue 69 of the patient's nostril 71, so as to continuously allow any excess respiratory gas supplied to the nasal cavity to be exhausted out therethrough. The leakage passageways 81 also continuously allow room air to flow inwardly therethrough in the event that additional air, for breathing by the patient in excess to the constant flow rate of the respiratory gas currently being supplied by the respiratory therapy system 40, is required during inhalation, e.g., at a peak negative pressure generated by the patient during inhalation. By this arrangement, the respiratory therapy system 40 is able to generate a sufficient resistance or back pressure within breathing passages of the patient, during exhalation, so that the breathing passages of the patient remain adequately open and/or inflated without significantly increasing the work required by the patient during each inhalation and exhalation breath.

As is known in the art, a normal human being typically has a blood O$_2$ concentration level of between 94% and 97%. One major respiratory problem plaguing numerous human beings worldwide is commonly known as sleep apnea, e.g., a condition where the O$_2$ concentration level in the patient's blood is about 88 percent or less.

The respiratory therapy system 40, according to the present invention, is readily able to treat both mild and moderate OSA and is also successful in treating severe OSA. During operation of the respiratory therapy system 40, the gas supply flow rate remains constant during the entire treatment period. That is, the respiratory therapy system 40 does not vary the flow rate of the supplied respiratory gas due to any variation in the leakage of the system as typically occurs with the prior art devices and systems. Nevertheless, the supplied flow rate of the supplied respiratory gas is sufficient to dilute and/or diffuse the CO$_2$ which is in the process of being exhaled by the patient, during an exhalation breath, while still maintaining an adequate resistance or back pressure in the patient's breathing passages so that the bronchi, the trachea, the lungs, etc., all remain sufficiently inflated during exhalation and upon commencement of a subsequent inhalation breath to thereby facilitate a more complete discharge or exhausting of the exhaust or byproduct gases, e.g., CO$_2$, from the patient while still maintaining a relatively low work of breathing for the patient during inhalation.

The respiratory therapy system 40 typically delivers the respiratory gas at a flow rate of between about 26 and about 60 liters per minute, preferable about 50 liters per minute at a pressure of between about 3 to 15 cm of water. Such flow conditions of the respiratory gas are generally adequate to create and maintain a sufficient back pressure in the breathing passages of the patient so that the breathing passages remain sufficiently open and do not collapse, during an exhalation breath of a patient. It is to be appreciated that if the breathing passages of the patient collapse, such collapse tends to prevent complete exhalation of CO$_2$ and/or any other patient byproduct gases and thereby traps the same within the breathing passages of the patient. Since, according to the present invention, the breathing passages of the patient are essentially prevented from collapsing and/or become sufficiently obstructed, during the exhalation, the normal gas exhaust airway passages, from the alveoli to the nasal cavity of the patient, remain sufficiently open, unconstricted and/or unobstructed during exhalation whereby any CO$_2$ and/or any other patient byproduct gases transferred to alveoli, from the blood stream of the patient, is able to flow along this normal gas exhaust airway passages and be exhaled by the patient during an exhalation breath.

Due to the higher delivery rates of the present invention, e.g., 26 to 60 liters per minute, for example, the respiratory therapy system 40 is prone to generate noise as the respiratory gas is supplied along the main respiratory gas supply line 16, the auxiliary gas supply lines 14, the supply arms 26 and/or the heads 72 to the patient. It is desirable to design the respiratory therapy system 40 to minimize generation of noise, during operation of the respiratory therapy system 40, to a noise level of less than 50 decibels or so and more preferably to reduce the generation of noise, during operation of the system, to a noise level approaching about 46 decibels or so. In order to achieve such a reduction in noise, it is important that the main respiratory gas supply line 16, the auxiliary respiratory gas supply lines 14, the supply arms 26 and the head 72 all have gradually bends, transitions, expansions and contractions along the respiratory gas flow path. That is, all of the respiratory gas supply lines, conduits, tubes, duct, channels, components, etc., must avoid any sharp, acute or right angle bends, turns or curvatures and also avoid any rapid expansion and contraction of the gas supply lines, conduits, tubes, duct, channels, components, etc.

The reduction in noise is particularly important as the nasal cannula 12, according to the present invention, is typically utilized at night while the patient is sleeping. To further reduce the noise, the transition from the supply arm 26 to the tubular extension 30 can have a gradual increase in dimension so that there is more gradual expansion of the respiratory gas that enters into the tubular extension 30 and this will further assist with reducing the noise associated with the respiratory gas conveyed to the patient.

Figure 11:
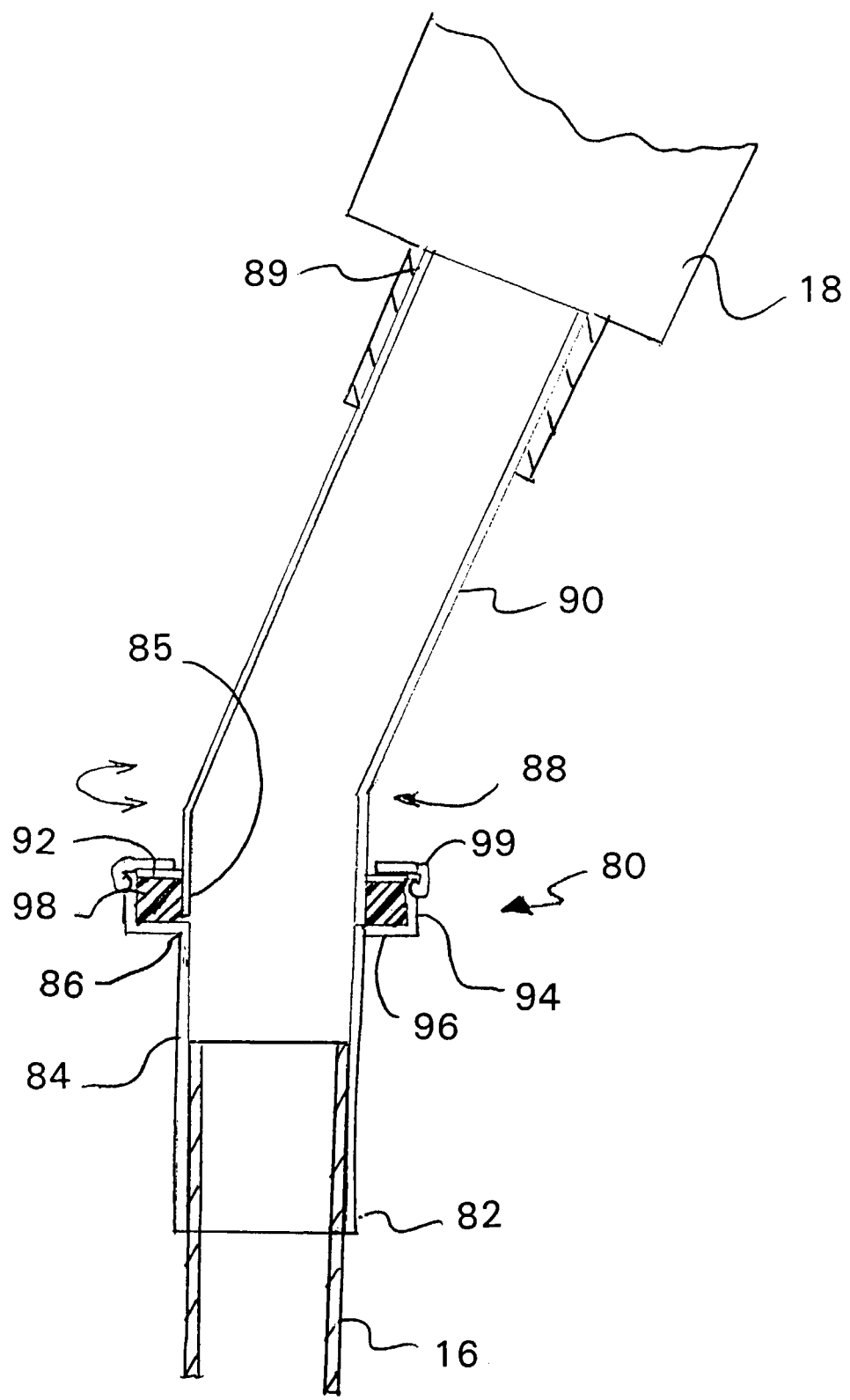
FIG. 11 is a diagrammatic cross sectional view of a swivel for use with the respiratory gas supply lines of the respiratory therapy system.

To further assist with providing comfort to a patient utilizing the respiratory therapy system 40, a 360 degree rotatable swivel 80 (see FIG. 11) may be provided, along the main respiratory gas supply line 16, for example, to facilitate rotation of the nasal cannula assembly 10 relative to a remainder of the respiratory therapy system 40. A preferred location for the swivel 80 is at a location closely adjacent the connection of the main respiratory gas supply line 16 with the connector 18 which, in turn, is coupled to the pair of auxiliary respiratory gas supply lines 14. A first end portion 82 of a stationary housing 84 of the swivel 80 encases or is received within the opening in the remote end of the main respiratory gas supply line 16. Preferably, the first end portion 82 of the stationary housing 84 is glued, welded, or otherwise fixedly secured or attached to the main respiratory gas supply line 16 to prevent inadvertent removal or disconnection therefrom.

The rotatable swivel 80 further includes a rotatable housing 90 which is has a first end 85 which is received by and encases the second end portion 86 of the stationary housing 84. A second end portion 89 of the rotatable housing 90 either encases or is directly received within an opening of the connector 18. Alternatively, a short supplemental section of the main respiratory gas supply line 16 (not shown) may interconnect the swivel 80 with the connector 18. An intermediate region of the rotatable housing 90, between the first and second end portions thereof, includes a small bend 88 of about 10 to about 45 degrees, preferably about 20 degrees or so.

The first end 85 of the rotatable housing 90 and the second end portion 86 of the stationary housing 84 each have a cooperating or mating components which retain the rotatable housing 90 in permanent engagement with the second end portion 86, e.g., by mating bearing surfaces or some other conventional arrangement, while still allowing relative rotation between those two components. The first end 85 of the rotatable housing 90 includes an integral shoulder 92 while the second end portion 86 of the stationary housing 84 includes an integral shroud 94 with a cooperating shoulder 96. A fluid tight gasket or seal 98 is sandwiched between the two shoulders 92, 96 to provide a seal which prevents any treating respiratory gas from leaking thereby. The shroud 94 encloses the gasket or seal 98 to minimize any damage thereto by the external environment. A snap locking ring 99 has a protrusion which engages with an annular recess provided in the exterior surface of the shroud 94 to captively retain the rotatable housing 90 on the stationary housing 84 while still allowing relative rotation between those two components.

The pair of auxiliary respiratory gas supply lines 14 are connected to an opposite end of the connector 18 and the swivel 80 permits rotation of the nasal cannula, the pair of auxiliary respiratory gas supply lines 14, the connector 18 and the rotatable housing 90 relative to the stationary housing 84, the main respiratory gas supply line 16 and a remainder of the respiratory therapy system 40. It is to be appreciated that a variety of modifications and changes may be made to the swivel 80, as would be readily apparent to those skilled in this art, without departing from the invention. Such modifications and changes are considered to be within the spirit and scope of the present invention.

Figure 12:
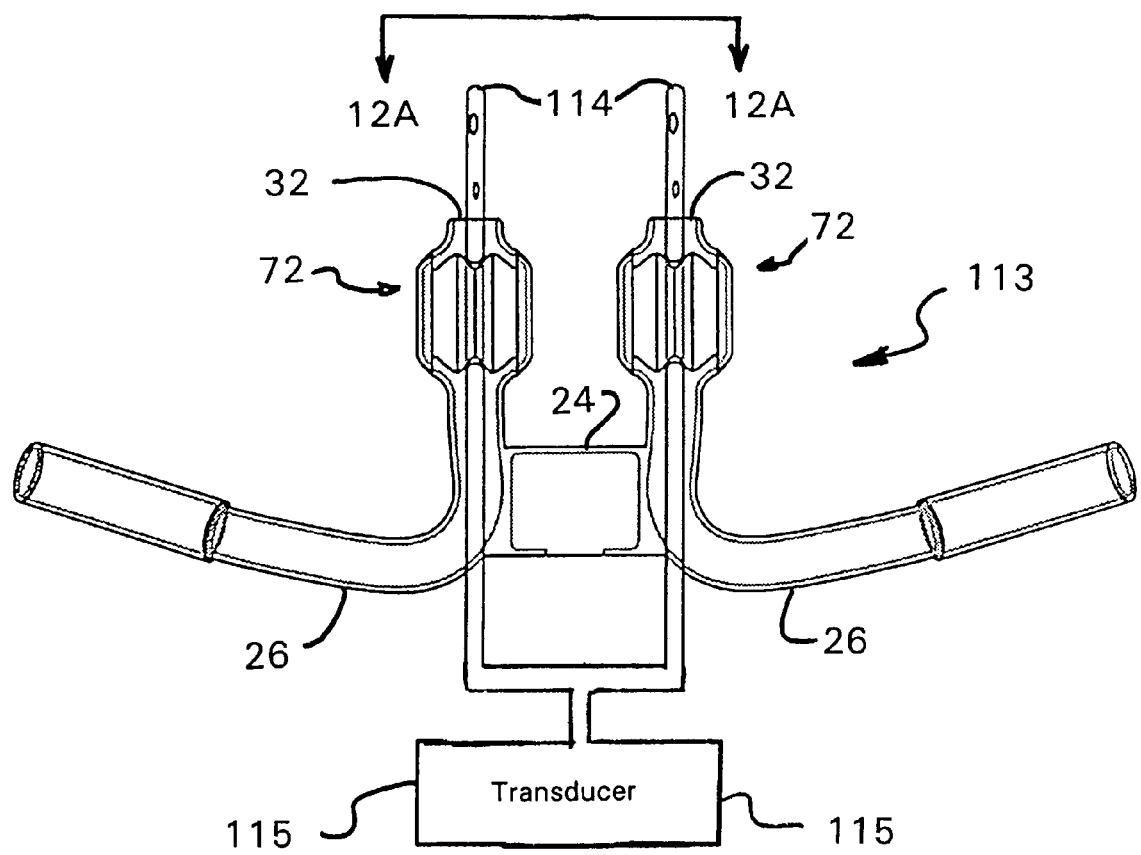
FIG. 12 is a front elevational view of a diagnostic tool incorporated into the cannula of the present invention.
Figure 12A:
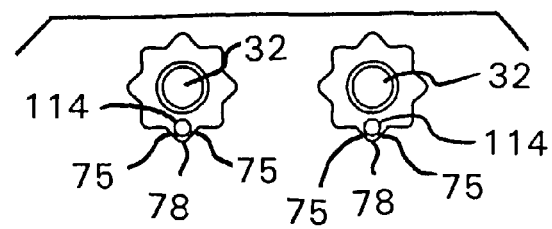
FIG. 12A is a diagrammatic view of the diagnostic tool of FIG. 12 in the direction of section line 12A-12A of FIG. 12.

With reference now to FIG. 12, a diagnostic tool 113 which is useful in measuring the nasal cavity pressure, during both patient inhalation and exhalation and is particularly suited for use in a sleep lab, will now be described. The diagnostic tool 113 generally comprises, for example, either a "large" or a "small" nasal cannula 12 discussed above with reference to FIGS. 9-10B but with a modification. The head 72 located at the ridge of each one of the ridges of the supply arms 26 supports a pressure sensing hollow tube or probe 114 which is either permanently secured thereto, e.g., glued or otherwise fastened thereto, or adjustably secured thereto in order to facilitate adjustment of the exposed length of the pressure sensing hollow tube or probe 114 relative to the respiratory gas discharge outlet 32. The pressure sensing hollow tube or probe 114 preferably enters through a rear end wall of the head 72 and passes within and through the interior space of the head 72 along an undersurface of one of the ridges 78 and two adjacent side surfaces 75 which converge at that ridge 78 (see FIG. 12A). The pressure sensing hollow tube or probe 114 preferably exits through a front end wall of the head 72 and extends parallel to the longitudinal axis of the ridge of the supply arm 26 away from the respiratory gas discharge outlet 32 deeper into the nasal cavity of the patient during use than a remainder of the nasal cannula. The exposed length of the pressure sensing hollow tube or probe 114, relative to the respiratory gas discharge outlet 32, typically ranges between 0.280 of an inch (0.71 cm) and 0.670 of an inch (1.70 cm), regardless of whether or not the pressure sensing hollow tube or probe 114 is permanently fixed to or adjustable relative to the head 72, and more preferably the exposed length of the pressure sensing hollow tube or probe 114, relative to the respiratory gas discharge outlet 32, is about 0.52 of an inch (1.32 cm). Due to such spacing or positioning of the pressure sensing probe 114, each one of the pressure sensing probes 114 is suitably located at desired position within the nasal cavity to more reliably detect a nasal cavity pressure reading. In the event that the position of the pressure sensing probe 114 relative to the respiratory gas discharge outlet 32 is adjustable, this tends to further facilitate more reliably detection of a pressure reading within the nasal cavity.

Figure 12B:
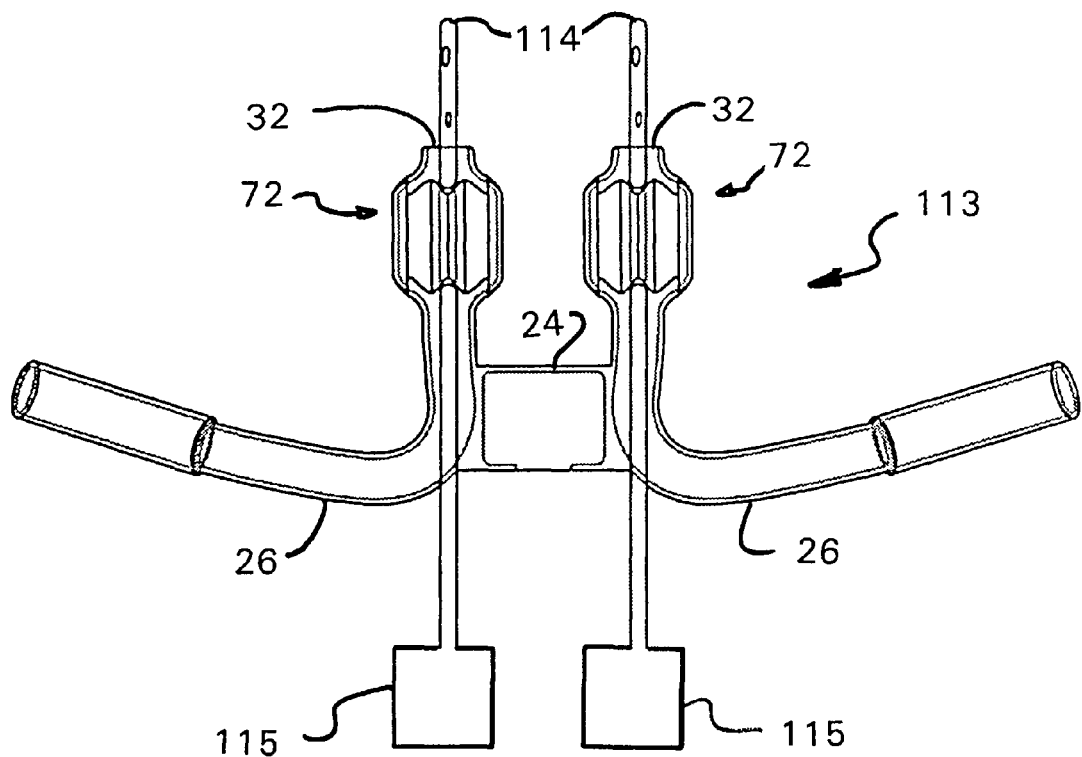
FIG. 12B is a front elevational view of the diagnostic tool of FIG. 12 showing each of the pressure sensing probe coupled to a separate pressure sensing device.

The opposite end of each one of the pressure sensing probe 114 are both coupled to supply a pressure reading to a single common pressure sensing device 115 (see FIG. 12), such as a transducer manufactured by Korr Medical Technologies, Inc. of Salt Lake City, Utah under the RSS 100 trademark/trade name or a handheld transducer manufactured by of Braebon Medical Corporation of Ogdensburg, N.Y. Alternatively, the opposite ends of each one of the pressure sensing probe 114 may each be coupled to a separate pressure sensing device 115 (see FIG. 12B) for measuring the pressure of each one of the nostril cavities of the patient. Preferably, the conduit or tubing, of the pressure sensing probe 114, has an outside diameter of between 0.068 of an inch (0.173 cm) and 0.070 of an inch (0.178 cm) or so in order to minimize any disruption of the respiratory gas flow through the interior space located within the head 72 of the nasal cannula assembly 10. As the pressure sensing probes 114 pass through the head 72, it generally does not disrupt or alter the normal achieved leakage interface between the exterior surface of the enlarged head 72 and the inwardly facing skin tissue 69 of the patient's nostril 71.

The diagnostic tool 113 is particularly adapted to be utilized to titrate and determine a desired back pressure within the breathing passages of the patient so that the breathing passages remain sufficiently open during both inhalation and exhalation. It is to be appreciated that the leakage passages 81, formed by each pair of adjacent side surfaces 75, diverging from a common elongate valley 76, and the inwardly facing skin tissue of the nostril 71, will typically vary from patient to patient, e.g., the leakage passages 81 for some patients will be larger or smaller than the leakage passages 81 of other patients. Further the breathing passageways, the bronchi, the trachea, the lungs, the lung capacity, etc., for each patient also vary widely.

During titration of a patient, typically the patient is permitted to sleep and is monitored with the diagnostic tool 113 while a respiratory gas is supplied to a patient at a first flow rate. The pressure within the nasal cavity of the patient is then determined by the pressure sensing probe 114 at this first respiratory gas flow rate. Depending upon the determined pressure and the detected breathing characteristics of the patient, the technician will then adjust the flow rate from the respiratory gas source 23 to vary, e.g., either increase or decrease, the flow rate of the respiratory gas being supplied to the patient. For each stepped increase or decrease of the respiratory gas flow rate, the technician continues to monitor the pressure generated within the nasal cavities of the patient and the breathing characteristics of the patient until the technician determines an optimum respiratory gas flow rate that achieves a desired back pressure within the breathing passages of the patient so that the patient breathes adequately, especially while the patient is sleeping.

Following the use of the diagnostic tool 113, the patient will then have a reasonably good indication of the pressure within the breathing passages of the patient which is required in order for the patient to breath adequately, e.g., treat sleep apnea. Once the patient is evaluated with the diagnostic tool 113, the patient can then be supplied with or obtain a supply of similarly sized cannulas for use by the patient. The patient can then install one of these similarly sized cannulas on his/her respiratory therapy system 40 and adjust the respiratory gas flow rate to this previously determined flow rate so that the patient will generate or create, within his/her breathing passageways and lungs, a sufficient back pressure and thereby facilitate a more complete exhalation or exhaustion of any $CO_2$ and/or any other patient byproduct gases which are contained in the lungs and removed from the blood stream. It is to be appreciated that the diagnostic tool 113 is not limited solely to CPAP applications but may be utilized for a wide variety of breathing and/or diagnostic applications.

Figure 13:
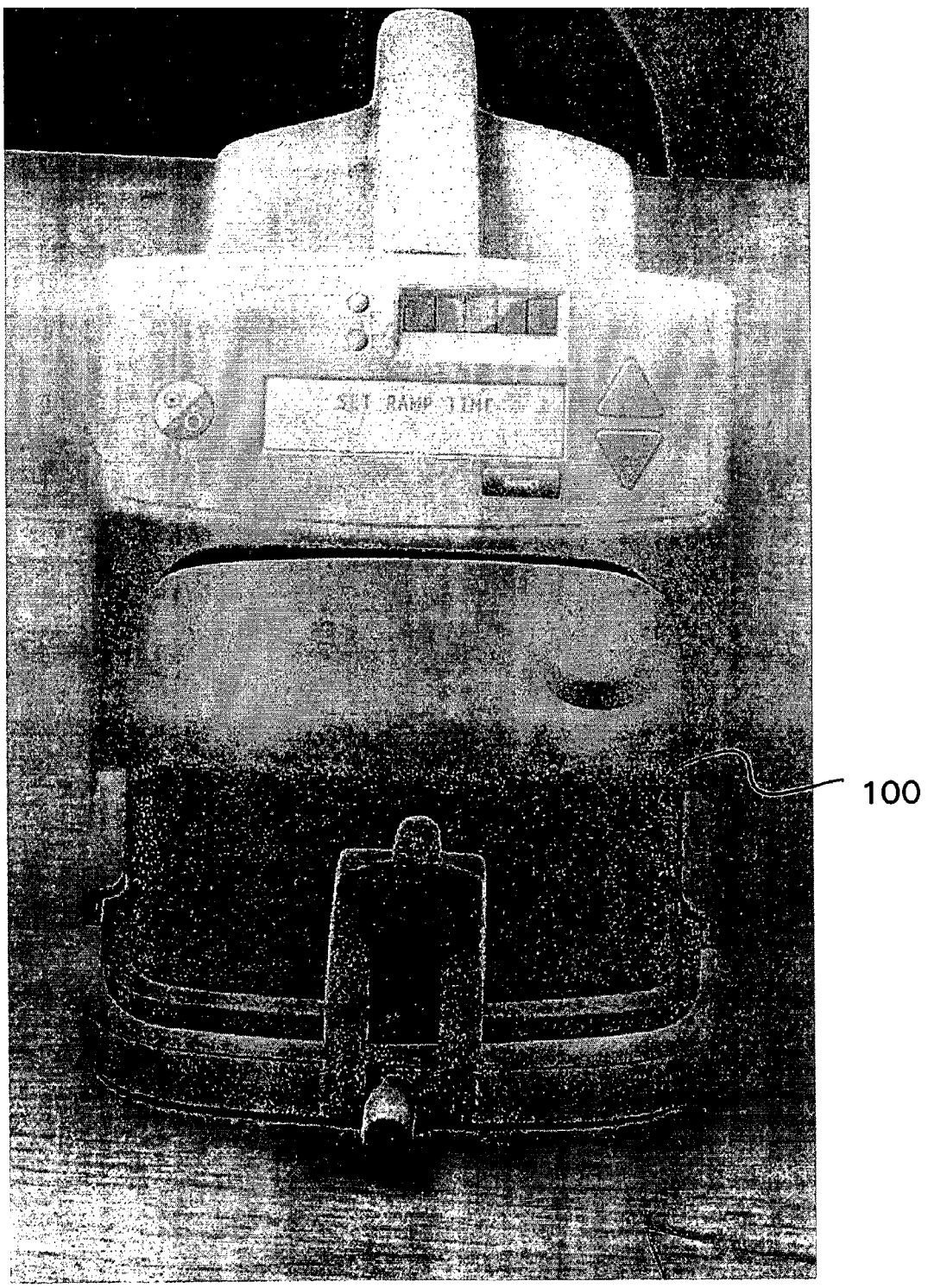
FIG. 13 is a diagrammatic view of a housing incorporating the various internal heating, moisturizing and control components of the respiratory therapy system.
Figure 13A:
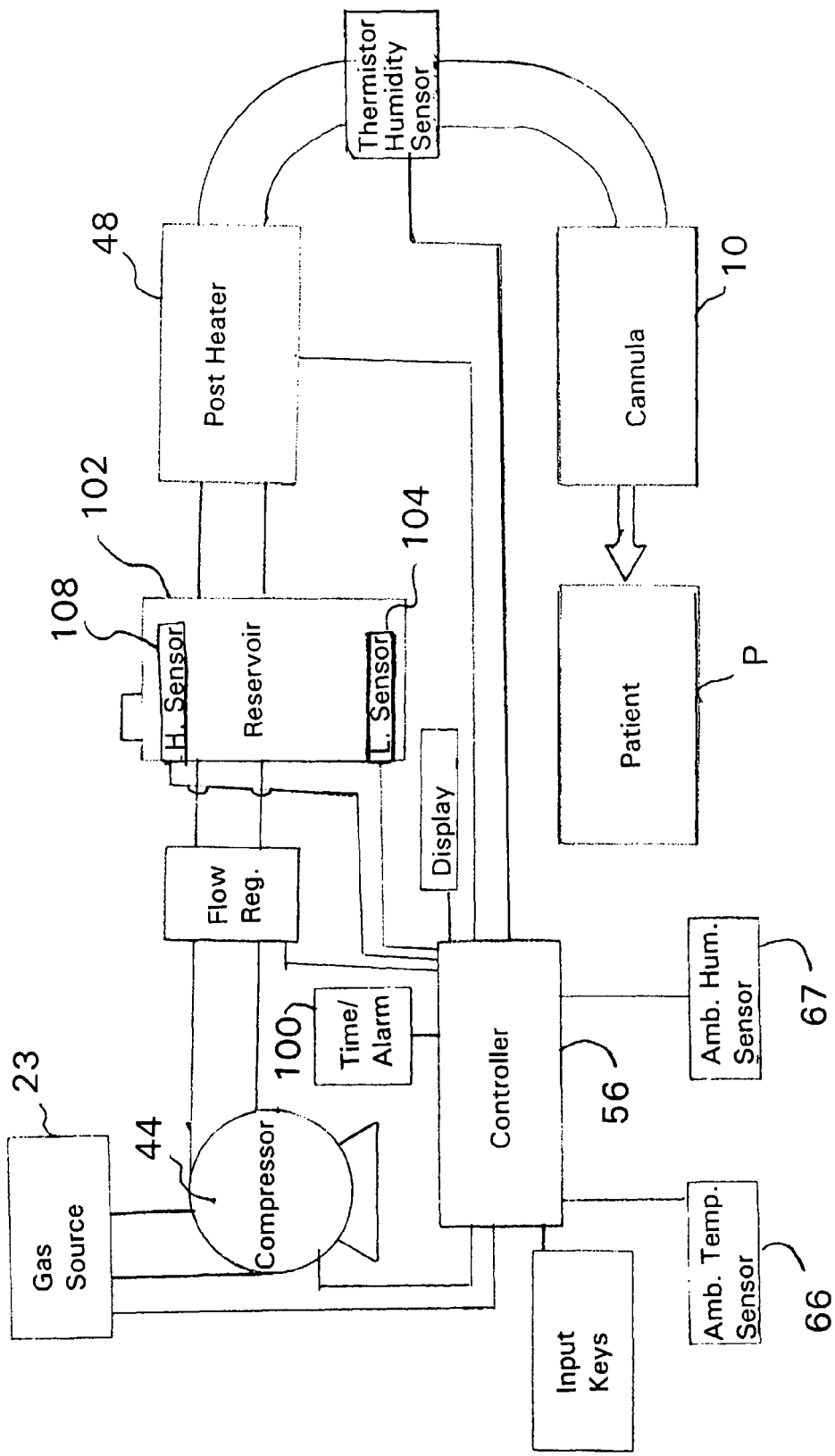
FIG. 13A is a diagrammatic view depicting the internal heating, moisturizing and control components of the housing of FIG. 13.

If desired, the respiratory therapy system 40 may be equipped with a clock 100 (only diagrammatically shown in FIGS. 13 and 13A) to display the current time to a patient using the respiratory therapy system 40. If desired, the clock may be equipped with an alarm to wake the patient at a desired wake up time in order to terminate supply or treatment of the respiratory gas after a desired treatment period. In addition, a water holding tank or reservoir 102 of the respiratory therapy system 40, for facilitate adding humidity to the respiratory gas prior to delivery of the same to the patient, may be equipped with a low water sensor 104 coupled to an indicator (not shown in the drawings) to provide either an auditory and/or a visual indication to the patient that the water level within the reservoir 102 is low and requires replenishment. The reservoir 102 may also be equipped with a high water sensor 108 coupled to an indicator (not shown in the drawings) to provide either an auditory and/or a visual indication to the patient that the water level in the reservoir is in excess of the amount of water required for efficient operation of the respiratory therapy system 40 and the patient should remove some water for more efficient operation of the respiratory therapy system 40. Lastly, the reservoir 102 may be equipped with a conventional water heater (not shown) to facilitate heating of the water contained therein. However, one problem associated with heating the water in the reservoir 102 is the generation of calcium carbonate which has a tendency to plate out on the inner surface of the reservoir 102. This may also lead to possible calcium carbonate plating of the water heater thereby requiring periodic servicing of the water heater. As each of the above features are conventional and well known in the art, a further detail description concerning the same is not provided.

Figure 14A:
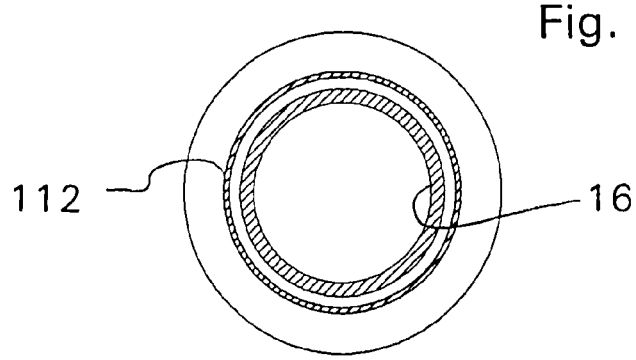
FIG. 14A is a diagrammatic cross section view along section line 14A-14A of FIG. 14.
Figure 14:
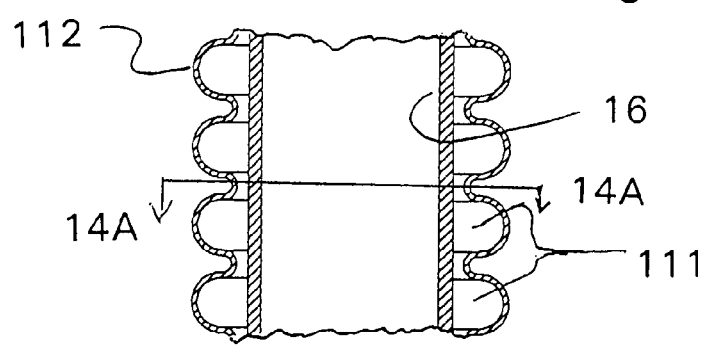
FIG. 14 is a diagrammatic longitudinal cross sectional view of a section of a corrugated tube or some conventional insulating wrap or material for the respiratory gas supply line.

To further insulate the heated and humidified respiratory gas from the ambient environment, the main respiratory gas supply line 16 and/or the auxiliary respiratory gas supply lines 14 may be covered by or encased within a plastic or corrugated tube or some conventional insulating wrap or material 112, e.g., a 10 mm corrugated tube 112. FIGS. 14 and 14A diagrammatically show the main respiratory gas supply line 16 surrounded by or encased within the insulating wrap or material 112. An insulating air pocket 111 is formed between the exterior surface of the main respiratory gas supply line 16 and the inwardly facing surface of the insulating wrap or material 112. The insulating wrap or material 112 helps to insulate the respiratory gas from the external environment of the respiratory therapy system 40 and help maintains the temperature of the respiratory gas substantially at the initially heated and supplied temperature and also minimizes the possibility of any humidity, added to the respiratory gas, condensing along the inner surface of either the main respiratory gas supply line 16, the connector 18, the swivel 80, the pair of auxiliary respiratory gas supply lines 14 and/or the nasal cannula.

As seen in FIG. 15, a slip loop or line tightening member 20 encases both of the auxiliary respiratory gas supply lines 14 to assist with applying sufficient tension to the auxiliary respiratory gas supply lines 14 to maintain the heads 72 of the supply arms 26 adequately positioned within the nostrils 71 of the patient. Preferably the line tightening member 20 will have flared or enlarged mouth 120 and 122, at both opposed ends thereof, but will have a smaller dimensioned intermediate section 124 for frictionally engaging with the exterior surface of both of the auxiliary respiratory gas supply lines 14. The intermediate section 124 is sized to have a sufficient interference fit with the exterior surface of the auxiliary respiratory gas supply lines 14 so as to be retained along the auxiliary respiratory gas supply lines 14 in any adjusted position. The frictional interference connection, between the intermediate section 124 of the line tightening member 20 and the exterior surface of the auxiliary respiratory gas supply lines 14, will maintain the line tightening member 20 at its adjusted position while the flared mouths 120, 122 allow the auxiliary respiratory gas supply lines 14 to extend away from the line tightening member 20 and move freely relative thereto without causing any sharp bend, kink or some other obstruction or constriction in either of the auxiliary respiratory gas supply lines 14.

An important aspect of the present invention relates to providing a constant flow of a respiratory gas to a patient while also controlling the amount of leakage escaping between the inwardly facing skin 69 of the nostril 71 of the patient and the exterior surface of the head 72 of each of the supply arms. This arrangement results in the breathing passageways of the patient being sufficiently inflated during the entire breathing process so that the passageways do not tend to constrict, collapse or otherwise obstruct relatively free breathing inhalation or exhalation of the patient.

Typically, the total combined length of the auxiliary supplied lines 14 and the main respiratory gas supply line 16, once connected with one another, extends for a combined length of between 3 feet and 50 feet or so, and more preferably have a total combined length of about 7 feet.

The supplied respiratory gas provides the necessary resistance to the patient, upon attempting an exhalation breath so that the breathing passageway and lungs remain sufficiently inflated and thus do not have a tendency to collapse, constrict or otherwise close or inhibit relatively free breathing during exhalation of the patient.

Due to the relatively high flow of the respiratory gas, the respiratory gas tends to dry out the nasal cavities and breathing passages of the patient. As noted above, in order to combat this, the respiratory gas is sufficiently humidified to a level approaching saturation while still avoiding condensation of the added moisture along the main respiratory gas line 16, the auxiliary respiratory gas supply lines 14, the swivel 80 and/or the connector 18.

In a preferred form of the invention, a temperature thermistor (not shown) may be located adjacent the connection of the main respiratory gas supply line 16 to the pair auxiliary respiratory gas supply lines 14, at or adjacent the connector 18, to determine the temperature of the respiratory gas just prior to the respiratory gas being split into two flow paths and conveyed to the nasal cannula assembly 10. This facilitates more accurate control of the temperature of the respiratory gas being delivered to the patient.

To further assist with controlling the temperature and/or humidity of the respiratory gas being delivered to the patient, the system 40 may be equipped with a conventional look-up table which has the relative humidities for different temperatures stored therein, i.e., it will be appreciated that the respiratory gas, depending upon its temperature, will have different relative humidities. The respiratory therapy system 40 can then utilize this stored temperature and/or humidity information to further optimize control of the humidity and temperature of the supplied respiratory gas during operation of the system. As such look-up tables and utilization thereof are conventional and well known in the art, a further detailed description concerning the same is not provided.

Figure 13B:
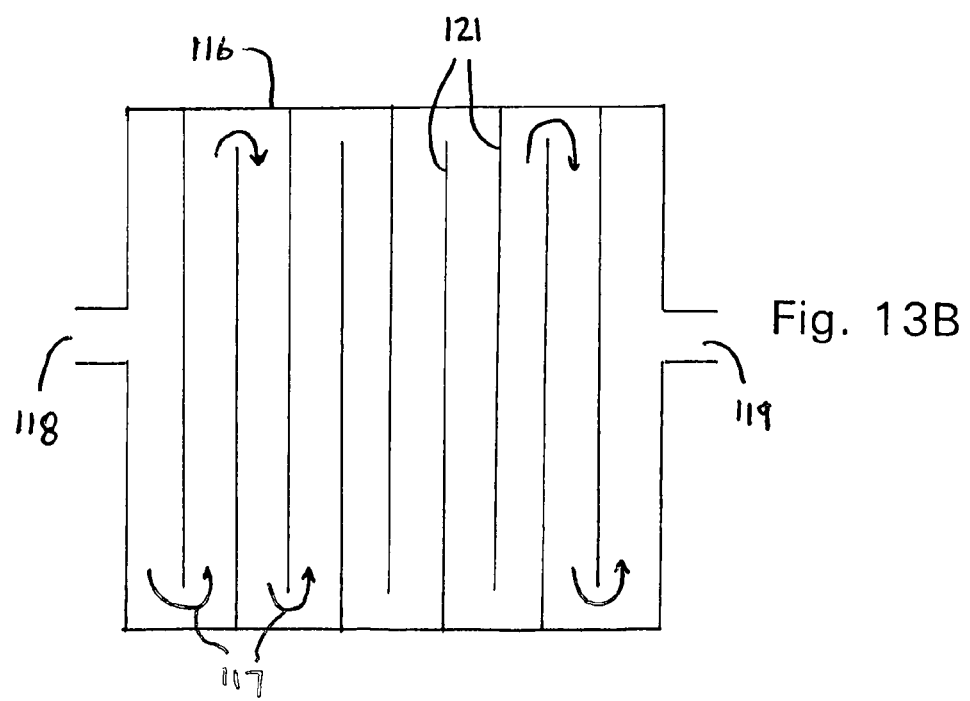
FIG. 13B is a diagrammatic cross sectional view of the post heater of FIG. 13.

To facilitate adding moisture to the respiratory gas, the respiratory gas is passed through a passover humidifier 116 (see FIG. 13B) where the respiratory gas passes around a serpentine or maze-like flow path 117 from an inlet 118 to an outlet 119 thereof around a plurality of the baffles 121 and an inwardly facing surface of an outer wall enclosing the passover humidifier 116. The respiratory gas, as it passes by, over and/or through the passover humidifier 116, is sufficiently humidified to a desired humidity. However, one problem associated with using tap water is the generation of calcium carbonate and/or other compounds which tend to plate out on and along the surface of the baffles 121 and/or the inner surface of the reservoir and could also lead to possible plating of calcium carbonate and/or other compounds thereon. If desired, as discussed above, the reservoir can be equipped with both high and low water level alarms to notify the patient when service in the reservoir is required.

The compressor supplies the respiratory gas to the reservoir where the respiratory gas will receive a sufficient quantity of moisture and is then passed to the post heater where the moisturized respiratory gas is then heated to a desired temperature, e.g., between 27° C. and 32° C. Thereafter, the heated and moisturized respiratory gas is then conveyed to the patient, via the auxiliary respiratory gas supply lines 14, where the heated and moisturized respiratory gas is then inhaled by the patient. The temperature of the post heater is controlled by a controller 56 which controls the temperature of the post heater so that the respiratory gas is heated to a desired temperature. If necessary, the controller can turn off the post heater entirely or shut it down if it becomes too hot due to the generation of excessive heat and then sound an alarm to notify the patient or other personnel that servicing of the post heater is required. The respiratory gas, after passing through the post heater, typically will have a relative humidity of between 70 and 95 cent while it is preferable for the respiratory gas to have a relative humidity of up to 85 percent.

With respect to heating of the respiratory gas, a post heating arrangement is preferred as it heats up and cools down relatively quickly thereby facilitating more accurate control of the temperature of the respiratory gas being supplied to the patient.

If desired, the respiratory therapy system may also include a respiratory gas metering device (not shown) which facilitates conservation of use of the respiratory gas during operation of the respiratory gas system. That is, the respiratory gas metering device will interrupt the constant flow of the respiratory gas to the patient for a brief period of time, e.g., between breath when the patient is neither inhaling or exhaling, in order to conserve use of the respiratory gas. As such respiratory gas metering device, for interrupting a constant flow of the respiratory gas to the patient for a brief period of time, is conventional and well known in the art, a further detail discussion concerning the same is not provided.

Since certain changes may be made in the above described respiratory therapy system without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A nasal cannula for supplying a respiratory gas to a patient, the nasal cannula comprising:

a pair of supply lines which each have a head adjacent a leading end thereof with a discharge opening therein for discharging a respiratory gas, and an opposite end of each of the pair of supply lines being connectable to a respiratory gas source;

wherein each head is formed integrally with and from the same material as the pair of supply line and each head comprises a leading tapered section and a trailing cylindrical section, the cylindrical section having a generally cylindrical surface which is sized to be snugly received and retained within one of the nasal cavities of the patient, each head has a maximum width dimension of between 0.345 of an inch (0.88 cm) and 0.70 of an inch (1.8 cm) and a length of between 0.30 of an inch (0.76 cm) and 0.60 of an inch (1.5 cm), an exterior surface of each head has a plurality elongate troughs formed therein, and each of the plurality of elongate troughs extends parallel to one another and is formed in the generally cylindrical surface of the head;

each of the plurality elongate troughs is formed by a pair of adjacent planar side surfaces which diverge away from a common elongate valley toward a pair of spaced apart but adjacent elongate ridges having maximum outside diameters coequal with the maximum outside diameter of each head to partially define one of the plurality of leakage passages, the plurality elongate troughs form, once inserted into the respective nasal cavity, a plurality of leakage passages, to facilitate exhausting of excess respiratory gas supplied to the patient through the leakage passage while maintaining a positive pressure within a respiratory passage of the patient at least during exhalation by the patient;

the pair of supply lines being connected with one another by a central bridge member; and opposed front and rear walls of at least one of the heads have an aligned aperture therein which facilitates passage of a pressure sensing probe through the head and into the nasal cavity of the patient.

2. The nasal cannula according to claim 1, wherein the exterior surface of the head has between six and eight elongate troughs formed therein which are equally spaced about a circumference of the head, and each of the elongate troughs partially defines one of the leakage passages in the head to facilitate exhausting of the excess respiratory gas and inhalation of any room air required by the patient.

3. The nasal cannula according to claim 1, wherein each of the plurality elongate troughs is formed by a pair of adjacent planar side surfaces which diverge away from a common elongate valley toward a pair of spaced apart but adjacent elongate ridges to partially define one of the plurality of leakage passages.

4. The nasal cannula according to claim 1, wherein each one of the leakage passages has a cross sectional open area of between 0.002 square inches (0.013 cm$^2$) and 0.0055 square inches (0.035 cm$^2$).

5. The nasal cannula according to claim 1, wherein an upper surface of the central bridge member is rounded to avoid any sharp edge that may contact with a nasal septum of the patient.

6. The nasal cannula according to claim 5, wherein the second end of each of the supply lines is coupled to an auxiliary respiratory gas supply line, and at least the second end of each of the supply lines is curved to pass beneath a patient's cheekbone area when the nasal cannula is donned by a patient.

7. The nasal cannula according to claim 1, wherein the supply lines and the heads are manufactured from a flexible material; and a second end of each of the supply lines bends away from one another.

8. The nasal cannula according to claim 1, wherein the central bridge member aligns the pair of supply lines parallel to one another to facilitate insertion of the heads, carried by the ridge of the pair of supply lines, within the nostrils of the patient, and each of the supply lines initially extends away from the central bridge member and then bends into a curved configuration having a radius of curvature of between 0.4 inch to 0.8 inch which creates a minimal pressure drop, turbulence and noise generation at a maximum flow rate.

9. A nasal cannula assembly for supplying a respiratory gas to a patient, the nasal cannula assembly comprising:

a pair of supply lines which each have a head adjacent a leading end thereof with a discharge opening therein for discharging a respiratory gas, and an opposite end of each of the pair of supply lines being connected to an auxiliary respiratory gas supply line; and a remote end of each of the auxiliary respiratory gas supply line is connected with a respiratory gas source for supplying the respiratory gas to the patient;

wherein each head is formed integrally with and from the same material as the pair of supply line and each head comprises a leading tapered section that communicates directly with a trailing cylindrical section, the cylindrical section being longer in axial length than the tapered section, the cylindrical section having a generally cylindrical surface which is sized to be snugly received and retained within one of the nasal cavities of the patient, an exterior surface of each head has a plurality elongate troughs formed therein, and each of the plurality of elongate troughs extends parallel to one another and is formed in the surface of the tapered section and the cylindrical section of the head, each head has a maximum width dimension of between 0.345 of an inch (0.88 cm) and 0.70 of an inch (1.8 cm) and a length of between 0.30 of an inch (0.76 cm) and 0.60 of an inch (1.5 cm);

the plurality elongate troughs form, once insert into the respective nasal cavity, a plurality of leakage passages, between a portion of inwardly facing nasal cavity skin of the patient and the plurality elongate troughs of the head, to facilitate exhausting of excess respiratory gas supplied to the patient through the leakage passage while maintaining a positive pressure within a respiratory passage of the patient at least during exhalation by the patient, each of the plurality elongate troughs is formed by a pair of adjacent planar side surfaces which diverge away from a common elongate valley toward a pair of spaced apart but adjacent elongate ridges having maximum outside diameters coequal with the maximum outside diameter of each head to partially define one of the plurality of leakage passages; and the pair of supply lines being connected with one another by a central bridge member; and opposed front and rear walls of at least one of the heads have an aligned aperture therein which facilitates passage of a pressure sensing probe through the head and into the nasal cavity of the patient.

10. The nasal cannula assembly according to claim 9, wherein the exterior surface of the head has between six and eight elongate troughs formed therein which are equally spaced about a circumference of the head, and each of the elongate troughs partially defines one of the leakage passages in the head to facilitate exhausting of the excess respiratory gas and inhalation of any room air required by the patient.

11. The nasal cannula assembly according to claim 9, wherein each of the plurality elongate troughs is formed by a pair of adjacent planar side surfaces which diverge away from a common elongate valley toward a pair of spaced apart but adjacent elongate ridges to partially define one of the plurality of leakage passages.

12. The nasal cannula assembly according to claim 9, wherein each one of the leakage passages has a cross sectional open area of between 0.002 square inches (0.013 cm$^2$) and 0.0055 square inches (0.035 cm$^2$).

13. The nasal cannula assembly according to claim 9, wherein each head has a maximum width dimension of between 0.345 of an inch (0.88 cm) and 0.70 of an inch (1.8 cm) and a length of between 0.30 of an inch (0.76 cm) and 0.60 of an inch (1.5 cm).

14. The nasal cannula assembly according to claim 9, wherein, the central bridge member is formed integral with and from a same material as the supply lines and the heads.

15. The nasal cannula assembly according to claim 9, wherein the nasal cannula is manufactured from a flexible material; and a second end of each of the supply lines bends away from one another and is curved.

16. The nasal cannula assembly according to claim 9, wherein the second end of each of the supply lines is coupled to an auxiliary respiratory gas supply line, and at least the second end of each of the supply lines is curved to pass beneath a patient's cheekbone area when the nasal cannula is donned by a patient, and the head defines an through aperture, radially spaced from an interior of the supply line and parallel to and spaced from the to the plurality of elongate troughs.

17. A nasal cannula for supplying a respiratory gas to a patient, the nasal cannula comprising:

a nasal cannula assembly having first and second cannula arms connectable to corresponding first and second supply lines, the supply lines being connectable to a respiratory gas source and each of the first and second cannula arms including an integral head at an end thereof with each head being insertable into a corresponding nasal passage of a patient, and each head including a discharge opening for providing a respiratory gas to the corresponding nasal passage of the patient, a central bridge member, located adjacent the heads, for aligning the pair of supply lines with one another and facilitating insertion of the heads within the corresponding nasal cavities of the patient, wherein a cylindrical exterior surface of each head has a maximum outside diameter sized so as to be snugly received and retained within one of the nasal cavities of the patient, the exterior surface of the head has a plurality elongate troughs formed therein so as to define a plurality of leakage passages which facilitate exhausting of excess respiratory gas through the leakage passages while maintaining a positive pressure within a respiratory passage of the patient at least during exhalation by the patient, and each of the plurality of elongate troughs extends parallel to one another and is formed in the generally cylindrical surface of the head, opposed front and rear walls of at least one of the heads have an aligned aperture therein which facilitates passage of a pressure sensing probe through the head and into the nasal cavity of the patient, each of the plurality elongate troughs is formed by a pair of adjacent planar side surfaces which diverge away from a common elongate valley toward a pair of spaced apart but adjacent elongate ridges having maximum outside diameters coequal with the maximum outside diameter of each head to partially define one of the plurality of leakage passages, and each of the first and second gas supply lines has a first portion curving outwards and upwards from a connection with the correspond one of the first and second cannula arms so as to follow a surface of a cheek of a patient along a path below a corresponding cheekbone of a patient to a first point in a region generally below an outer corner of a corresponding eye of a patient, each gas supply line having a second portion extending from the first point that curves downwards and inwards along the surface of the surface of the cheek of a patient along a jawline of a patient to a second point between the outer corner of the corresponding eye of a patient and a corresponding ear of a patient, each gas supply line having a third portion extending from the second point that curves inward below the corresponding jawline of a patient and forward along a corresponding side of a through of a patient to a third point located below a chin of a patient and near a mid-line of a patient's face, and each gas supply line having a fourth portion extending from the third point and curving toward the other gas supply line and downwards to a connector for connecting the first and second gas lines to a common gas supply line.

* * * * *